US010099022B2

(12) United States Patent
Eicher et al.

(10) Patent No.: US 10,099,022 B2
(45) Date of Patent: Oct. 16, 2018

(54) NEBULIZER

(71) Applicant: Boehringer Ingelheim International GmbH, Ingelheim am Rhein (DE)

(72) Inventors: Joachim Eicher, Ingelheim am Rhein (DE); Josef Gatz, Moosbach (DE); Frank Herrmann, Duisburg (DE); Hubert Hoelz, Oberheimbach (DE); Andree Jung, Idar-Oberstein (DE); Martin Meisenheimer, Appenheim (DE); Markus Mueller, Cham (DE); Alfred Von Schuckmann, Kevelaer (DE); Herbert Wachtel, Ingelheim am Rhein (DE); Robert Gerhard Winkler, Aschaffenburg (DE); Gilbert Wuttke, Ingelheim am Rhein (DE); Jochen Ziegler, Heidelberg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 657 days.

(21) Appl. No.: 14/703,125

(22) Filed: May 4, 2015

(65) Prior Publication Data

US 2015/0320947 A1    Nov. 12, 2015

(30) Foreign Application Priority Data

May 7, 2014   (EP) .................................... 14001603

(51) Int. Cl.
*A61M 11/00* (2006.01)
*A61M 15/00* (2006.01)
*B05B 11/00* (2006.01)

(52) U.S. Cl.
CPC ........ *A61M 15/0081* (2014.02); *A61M 11/00* (2013.01); *A61M 11/007* (2014.02);
(Continued)

(58) Field of Classification Search
CPC .......... A61M 15/0081; A61M 15/0036; A61M 15/0021; A61M 15/0026; A61M 11/007;
(Continued)

(56) References Cited

U.S. PATENT DOCUMENTS

| 1,828,864 A | 10/1931 | Hopkins |
| 2,015,970 A | 10/1935 | Schoene |

(Continued)

FOREIGN PATENT DOCUMENTS

| AU | 2005201364 A1 | 7/2006 |
| CA | 1094549 A | 1/1981 |

(Continued)

OTHER PUBLICATIONS

"Activate". Collins English Dictionary, London: Collins, 2000, 2 pages. [Retrieved at http://search.credoreference.com/content/entry/hcengdict/activate/0 on Jun. 12, 2014].

(Continued)

*Primary Examiner* — Steven Douglas
(74) *Attorney, Agent, or Firm* — Philip I. Datlow

(57) ABSTRACT

A nebulizer and a container with a fluid for such a nebulizer are described, the container comprising an indicator device fixedly mounted on the bottom of the container, the indicator device stopping further use of the container in a locked state when a predetermined number of uses has been reached or exceeded, and when the nebulizer is partially opened, it is blocked against further use, and after replacement of the container including the indicator device, the nebulizer can be used again.

30 Claims, 20 Drawing Sheets

(52) U.S. Cl.
CPC ...... *A61M 15/004* (2014.02); *A61M 15/0021* (2014.02); *A61M 15/0026* (2014.02); *A61M 15/0035* (2014.02); *A61M 15/0036* (2014.02); *A61M 15/0041* (2014.02); *A61M 15/0065* (2013.01); *A61M 15/0071* (2014.02); *A61M 15/0073* (2014.02); *B05B 11/0054* (2013.01); *B05B 11/308* (2013.01); *A61M 2202/0468* (2013.01); *A61M 2205/273* (2013.01); *A61M 2205/583* (2013.01); *A61M 2205/586* (2013.01); *A61M 2207/10* (2013.01)

(58) Field of Classification Search
CPC .......... A61M 15/0065; A61M 15/0073; A61M 15/0041; A61M 15/0035; A61M 15/004; A61M 15/0071; A61M 11/00; A61M 2205/583; A61M 2207/10; A61M 2205/586; A61M 2205/273; A61M 2202/0468; A61M 2202/0007; B05B 11/308
See application file for complete search history.

(56) References Cited

U.S. PATENT DOCUMENTS

| | | |
|---|---|---|
| 2,127,401 A | 8/1938 | Gillican |
| 2,161,071 A | 6/1939 | McGrath et al. |
| 2,321,428 A | 6/1943 | Schloz |
| 2,329,311 A | 9/1943 | Waters |
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,354,883 A | 11/1967 | Southerland |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Fedit |
| 3,580,249 A | 5/1971 | Takaoka |
| 3,590,557 A | 7/1971 | Vogel |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,802,604 A | 4/1974 | Morane et al. |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,456,016 A | 6/1984 | Nowacki et al. |
| 4,467,965 A | 8/1984 | Skinner |
| 4,476,116 A | 10/1984 | Anik |
| 4,515,586 A | 5/1985 | Mendenhall et al. |
| 4,516,967 A | 5/1985 | Kopfer |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A | 9/1989 | Dreinhoff |
| 4,885,164 A | 12/1989 | Thurow |
| 4,905,450 A | 3/1990 | Hansen et al. |
| 4,926,613 A | 5/1990 | Hansen |
| 4,951,661 A | 8/1990 | Sladek |
| 4,952,310 A | 8/1990 | McMahan et al. |
| 4,964,540 A | 10/1990 | Katz |
| RE33,444 E | 11/1990 | Lerner |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A | 10/1992 | Marks et al. |
| 5,174,366 A | 12/1992 | Nagakura et al. |
| 5,207,217 A | 5/1993 | Cocozza et al. |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,394,866 A | 3/1995 | Ritson et al. |
| 5,408,994 A | 4/1995 | Wass et al. |
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |
| 5,503,869 A | 4/1996 | Van Oort |
| 5,509,404 A | 4/1996 | Lloyd et al. |
| 5,518,147 A | 5/1996 | Peterson et al. |
| 5,533,994 A | 7/1996 | Meyer |
| 5,541,569 A | 7/1996 | Jang |
| 5,544,646 A | 8/1996 | Lloyd et al. |
| 5,547,094 A | 8/1996 | Bartels et al. |
| 5,569,191 A | 10/1996 | Meyer |
| 5,574,006 A | 11/1996 | Yanagawa |
| 5,579,760 A | 12/1996 | Kohler |
| 5,593,069 A | 1/1997 | Jinks |

(56) References Cited

U.S. PATENT DOCUMENTS

| | | |
|---|---|---|
| 5,599,297 A | 2/1997 | Chin et al. |
| 5,603,943 A | 2/1997 | Yanagawa |
| 5,614,172 A | 3/1997 | Geimer |
| 5,622,162 A | 4/1997 | Johansson et al. |
| 5,622,163 A | 4/1997 | Jewett et al. |
| 5,643,868 A | 7/1997 | Weiner et al. |
| 5,662,098 A | 9/1997 | Yoshida |
| 5,662,271 A | 9/1997 | Weston et al. |
| 5,676,930 A | 10/1997 | Jager et al. |
| 5,685,846 A | 11/1997 | Michaels, Jr. |
| 5,697,242 A | 12/1997 | Halasz et al. |
| 5,709,202 A | 1/1998 | Lloyd et al. |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A | 7/1998 | Alband |
| 5,782,345 A | 7/1998 | Guasch et al. |
| 5,827,262 A | 10/1998 | Neftel et al. |
| 5,829,435 A | 11/1998 | Rubsamen et al. |
| 5,833,088 A | 11/1998 | Kladders et al. |
| 5,848,588 A | 12/1998 | Foley et al. |
| 5,868,287 A | 2/1999 | Kurokawa et al. |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A | 8/1999 | Lloyd et al. |
| 5,935,101 A | 8/1999 | Kato et al. |
| 5,941,244 A | 8/1999 | Yamazaki et al. |
| 5,950,016 A | 9/1999 | Tanaka |
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,110,247 A | 8/2000 | Birmingham et al. |
| 6,116,233 A | 9/2000 | Denyer et al. |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A | 11/2000 | Cirrillo et al. |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 | 8/2001 | de Pous et al. |
| 6,302,101 B1 | 10/2001 | Py |
| 6,315,173 B1 | 11/2001 | Di Giovanni et al. |
| 6,319,943 B1 | 11/2001 | Joshi et al. |
| 6,341,718 B1 | 1/2002 | Schilthuizen et al. |
| 6,349,856 B1 | 2/2002 | Chastel |
| 6,352,152 B1 | 3/2002 | Anderson et al. |
| 6,352,181 B1 | 3/2002 | Eberhard et al. |
| 6,363,932 B1 | 4/2002 | Forchione et al. |
| 6,375,048 B1 | 4/2002 | van der Meer et al. |
| 6,392,962 B1 | 5/2002 | Wyatt |
| 6,395,331 B1 | 5/2002 | Yan et al. |
| 6,401,710 B1 | 6/2002 | Scheuch et al. |
| 6,401,987 B1 | 6/2002 | Oechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B1 | 4/2003 | Smith et al. |
| 6,548,647 B2 | 4/2003 | Dietz et al. |
| 6,550,477 B1 | 4/2003 | Casper et al. |
| 6,565,743 B1 | 5/2003 | Poirier et al. |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen et al. |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 | 1/2004 | Rand et al. |
| 6,685,691 B1 | 2/2004 | Freund et al. |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 | 9/2004 | Davies et al. |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 | 5/2005 | Crowder et al. |
| 6,890,517 B2 | 5/2005 | Drechsel et al. |
| 6,915,901 B2 | 7/2005 | Feinberg et al. |
| 6,929,004 B1 | 8/2005 | Bonney et al. |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 | 7/2009 | Mori |
| 7,571,722 B2 | 8/2009 | Wuttke et al. |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 | 2/2010 | Zierenberg et al. |
| 7,681,811 B2 | 3/2010 | Geser et al. |
| 7,686,014 B2 | 3/2010 | Boehm et al. |
| 7,717,299 B2 | 5/2010 | Greiner-Perth |
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |

(56) References Cited

U.S. PATENT DOCUMENTS

| | | |
|---|---|---|
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |
| 7,896,264 B2 | 3/2011 | Eicher et al. |
| 7,980,243 B2 | 7/2011 | Hochrainer |
| 7,994,188 B2 | 8/2011 | Disse |
| 8,062,626 B2 | 11/2011 | Freund et al. |
| 8,167,171 B2 | 5/2012 | Moretti |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 | 2/2014 | Leak et al. |
| 8,656,910 B2 | 2/2014 | Boeck et al. |
| 8,733,341 B2 | 5/2014 | Boeck et al. |
| 8,734,392 B2 | 5/2014 | Stadelhofer |
| 8,950,393 B2 | 2/2015 | Holakovsky et al. |
| 8,960,188 B2 | 2/2015 | Bach et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 2001/0008632 A1 | 7/2001 | Freund et al. |
| 2001/0028308 A1 | 10/2001 | De La Huerga |
| 2001/0032643 A1 | 10/2001 | Hochrainer et al. |
| 2001/0035182 A1 | 11/2001 | Rubin et al. |
| 2002/0000225 A1 | 1/2002 | Schuler et al. |
| 2002/0007155 A1 | 1/2002 | Freund et al. |
| 2002/0046751 A1 | 4/2002 | MacRae et al. |
| 2002/0060255 A1 | 5/2002 | Benoist |
| 2002/0074429 A1 | 6/2002 | Hettrich et al. |
| 2002/0079285 A1 | 6/2002 | Jansen et al. |
| 2002/0092523 A1 | 7/2002 | Connelly et al. |
| 2002/0111363 A1 | 8/2002 | Drechsel et al. |
| 2002/0129812 A1 | 9/2002 | Litherland et al. |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0085254 A1 | 5/2003 | Katooka et al. |
| 2003/0098023 A1 | 5/2003 | Drachmann et al. |
| 2003/0106827 A1 | 6/2003 | Cheu et al. |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0209238 A1 | 11/2003 | Peters et al. |
| 2003/0226907 A1 | 12/2003 | Geser et al. |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1 | 4/2004 | Sirejacob |
| 2004/0069799 A1 | 4/2004 | Gee et al. |
| 2004/0092428 A1 | 5/2004 | Chen et al. |
| 2004/0094147 A1 | 5/2004 | Schyra et al. |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0231667 A1 | 11/2004 | Horton et al. |
| 2005/0028815 A1 | 2/2005 | Deaton et al. |
| 2005/0028816 A1 | 2/2005 | Fishman et al. |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Nuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1 | 11/2005 | Zierenberg et al. |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268909 A1 | 12/2005 | Bonney et al. |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1 | 7/2006 | Lee et al. |
| 2006/0196500 A1 | 9/2006 | Hochrainer et al. |
| 2006/0225734 A1 | 10/2006 | Sagaser et al. |
| 2006/0239930 A1 | 10/2006 | Lamche et al. |
| 2006/0279588 A1 | 12/2006 | Yearworth et al. |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |
| 2007/0062518 A1 | 3/2007 | Geser et al. |
| 2007/0062519 A1 | 3/2007 | Wuttke et al. |
| 2007/0062979 A1 | 3/2007 | Dunne |
| 2007/0090205 A1 | 4/2007 | Kunze et al. |
| 2007/0090576 A1 | 4/2007 | Geser et al. |
| 2007/0107720 A1 | 5/2007 | Boeck et al. |
| 2007/0119449 A1 | 5/2007 | Boehm et al. |
| 2007/0137643 A1 | 6/2007 | Bonney et al. |
| 2007/0163574 A1 | 7/2007 | Rohrschneider et al. |
| 2007/0183982 A1 | 8/2007 | Berkel et al. |
| 2007/0210121 A1 | 9/2007 | Stadelhofer et al. |
| 2007/0221211 A1 | 9/2007 | Sagalovich |
| 2007/0272763 A1 | 11/2007 | Dunne et al. |
| 2007/0298116 A1 | 12/2007 | Bechtold-Peters et al. |
| 2008/0017192 A1 | 1/2008 | Southby et al. |
| 2008/0029085 A1 | 2/2008 | Lawrence et al. |
| 2008/0083408 A1 | 4/2008 | Hodson et al. |
| 2008/0092885 A1 | 4/2008 | von Schuckmann |
| 2008/0173669 A1 | 7/2008 | Pocock |
| 2008/0197045 A1 | 8/2008 | Metzger et al. |
| 2008/0249459 A1 | 10/2008 | Godfrey et al. |
| 2008/0265198 A1 | 10/2008 | Warby |
| 2008/0283553 A1 | 11/2008 | Cox et al. |
| 2008/0308580 A1 | 12/2008 | Gaydos et al. |
| 2009/0032427 A1 | 2/2009 | Cheu et al. |
| 2009/0060764 A1 | 3/2009 | Mitzlaff et al. |
| 2009/0075990 A1 | 3/2009 | Schmidt |
| 2009/0114215 A1 | 5/2009 | Boeck et al. |
| 2009/0166379 A1 | 7/2009 | Wright et al. |
| 2009/0170839 A1 | 7/2009 | Schmidt |
| 2009/0185983 A1 | 7/2009 | Freund et al. |
| 2009/0197841 A1 | 8/2009 | Kreher et al. |
| 2009/0202447 A1 | 8/2009 | Kreher et al. |
| 2009/0221626 A1 | 9/2009 | Schmidt |
| 2009/0235924 A1 | 9/2009 | Holakovsky et al. |
| 2009/0272664 A1 | 11/2009 | Marshall et al. |
| 2009/0293870 A1 | 12/2009 | Brunnberg et al. |
| 2009/0306065 A1 | 12/2009 | Schmidt |
| 2009/0308772 A1 | 12/2009 | Abrams |
| 2009/0314287 A1 | 12/2009 | Spallek et al. |
| 2009/0317337 A1 | 12/2009 | Schmidt |
| 2010/0018524 A1 | 1/2010 | Jinks et al. |
| 2010/0018997 A1 | 1/2010 | Faneca Llesera |
| 2010/0044393 A1 | 2/2010 | Moretti |
| 2010/0056559 A1 | 3/2010 | Schmelzer et al. |
| 2010/0084531 A1 | 4/2010 | Schuchman |
| 2010/0144784 A1 | 6/2010 | Schmelzer et al. |
| 2010/0168710 A1 | 7/2010 | Braithwaite |
| 2010/0237102 A1 | 9/2010 | Margheritis |
| 2010/0242557 A1 | 9/2010 | Spreitzer et al. |

(56) References Cited

U.S. PATENT DOCUMENTS

| | | |
|---|---|---|
| 2010/0242954 A1 | 9/2010 | Hahn et al. |
| 2011/0005517 A1 | 1/2011 | Boeck et al. |
| 2011/0011393 A1 | 1/2011 | Geser |
| 2011/0041842 A1 | 2/2011 | Bradshaw et al. |
| 2011/0168175 A1 | 7/2011 | Dunne et al. |
| 2011/0239594 A1 | 10/2011 | Nottingham et al. |
| 2011/0268668 A1 | 11/2011 | Lamche et al. |
| 2011/0277753 A1 | 11/2011 | Dunne et al. |
| 2011/0290239 A1 | 12/2011 | Bach et al. |
| 2011/0290242 A1 | 12/2011 | Bach et al. |
| 2011/0290243 A1 | 12/2011 | Bach et al. |
| 2012/0090603 A1 | 4/2012 | Dunne et al. |
| 2012/0132199 A1 | 5/2012 | Kiesewetter |
| 2012/0138049 A1 | 6/2012 | Wachtel |
| 2012/0138713 A1 | 6/2012 | Schuy et al. |
| 2012/0260913 A1 | 10/2012 | Bach et al. |
| 2012/0325204 A1 | 12/2012 | Holakovsky et al. |
| 2013/0012908 A1 | 1/2013 | Yeung |
| 2013/0056888 A1 | 3/2013 | Holakovsky et al. |
| 2013/0125880 A1 | 5/2013 | Holakovsky et al. |
| 2013/0125881 A1 | 5/2013 | Holakovsky et al. |
| 2013/0126389 A1 | 5/2013 | Holakovsky et al. |
| 2013/0206136 A1 | 8/2013 | Herrmann et al. |
| 2013/0269687 A1 | 10/2013 | Besseler et al. |
| 2014/0121234 A1 | 5/2014 | Kreher et al. |
| 2014/0190472 A1 | 7/2014 | Holakovsky et al. |
| 2014/0228397 A1 | 8/2014 | Schmelzer et al. |
| 2014/0331994 A1 | 11/2014 | Holakovsky et al. |
| 2015/0040890 A1 | 2/2015 | Besseler et al. |
| 2015/0040893 A1 | 2/2015 | Besseler et al. |
| 2015/0041558 A1 | 2/2015 | Besseler et al. |
| 2015/0114387 A1 | 4/2015 | Bach et al. |
| 2015/0122247 A1 | 5/2015 | Besseler et al. |
| 2015/0258021 A1 | 9/2015 | Kreher et al. |
| 2015/0306087 A1 | 10/2015 | Schmelzer et al. |
| 2015/0320948 A1 | 11/2015 | Eicher et al. |
| 2016/0095992 A1 | 4/2016 | Wachtel |

FOREIGN PATENT DOCUMENTS

| | | |
|---|---|---|
| CA | 2233981 A1 | 4/1997 |
| CA | 2237853 A1 | 6/1997 |
| CA | 2251828 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101141993 A | 3/2008 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 19902844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289332 A1 | 11/1988 |
| EP | 0289336 A2 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0735048 A1 | 10/1996 |
| EP | 0778221 A1 | 6/1997 |
| EP | 0845253 A2 | 6/1998 |
| EP | 0845265 A1 | 6/1998 |
| EP | 0860210 A2 | 8/1998 |
| EP | 0916428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1521609 A2 | 4/2005 |
| EP | 1535643 A1 | 6/2005 |
| EP | 1595564 A1 | 11/2005 |
| EP | 1595822 A1 | 11/2005 |
| EP | 1726324 A1 | 11/2006 |
| EP | 1736193 A1 | 12/2006 |
| EP | 1795221 A1 | 6/2007 |
| EP | 1813548 A1 | 8/2007 |
| EP | 2135632 A1 | 12/2009 |
| ES | 2262348 T3 | 11/2006 |
| FR | 2505688 A1 | 11/1982 |
| FR | 2604363 A1 | 4/1988 |
| FR | 2673608 A1 | 9/1992 |
| FR | 2756502 A1 | 6/1998 |
| GB | 1524431 A | 9/1978 |
| GB | 2101020 A | 1/1983 |
| GB | 2279273 A | 1/1995 |
| GB | 2291135 A | 1/1996 |
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 | 7/2008 |
| JP | S5684246 A | 7/1981 |
| JP | H01288265 A | 11/1989 |
| JP | H0228121 A | 1/1990 |
| JP | H057246 | 2/1993 |
| JP | H0553470 A | 3/1993 |
| JP | H06312019 A | 11/1994 |
| JP | H07118164 A | 5/1995 |
| JP | H07118166 A | 5/1995 |
| JP | 07323086 A | 12/1995 |
| JP | H08277226 A | 10/1996 |
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 2003511212 A | 3/2003 |
| JP | 2003299717 A | 10/2003 |
| JP | 2004502502 A | 1/2004 |
| JP | 2004097617 A | 4/2004 |
| JP | 2005511210 A | 4/2005 |
| JP | 2005144459 A | 6/2005 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541808 A | 11/2008 |

(56) References Cited

FOREIGN PATENT DOCUMENTS

| | | |
|---|---|---|
| JP | 2010526620 A | 8/2010 |
| JP | 2010540371 A | 12/2010 |
| WO | 198100674 A1 | 3/1981 |
| WO | 198200785 A1 | 3/1982 |
| WO | 198300288 A1 | 2/1983 |
| WO | 198303054 A1 | 9/1983 |
| WO | 198605419 A1 | 9/1986 |
| WO | 198706137 A1 | 10/1987 |
| WO | 198803419 A1 | 5/1988 |
| WO | 198900889 A1 | 2/1989 |
| WO | 198900947 A1 | 2/1989 |
| WO | 198902279 A1 | 3/1989 |
| WO | 198903672 A1 | 5/1989 |
| WO | 198903673 A1 | 5/1989 |
| WO | 198905139 A1 | 6/1989 |
| WO | 199009780 A1 | 9/1990 |
| WO | 199009781 A1 | 9/1990 |
| WO | 1991014468 A1 | 10/1991 |
| WO | 199206704 A1 | 4/1992 |
| WO | 199217231 A1 | 10/1992 |
| WO | 199221332 A1 | 12/1992 |
| WO | 199222286 | 12/1992 |
| WO | 1993013737 A1 | 7/1993 |
| WO | 199325321 A1 | 12/1993 |
| WO | 1993024164 A1 | 12/1993 |
| WO | 1994007607 A1 | 4/1994 |
| WO | 199417822 A1 | 8/1994 |
| WO | 199425371 A1 | 11/1994 |
| WO | 199427653 A2 | 12/1994 |
| WO | 199503034 A1 | 2/1995 |
| WO | 1995032015 A1 | 11/1995 |
| WO | 199600050 A1 | 1/1996 |
| WO | 1996006011 A2 | 2/1996 |
| WO | 199606581 A1 | 3/1996 |
| WO | 199623522 A1 | 8/1996 |
| WO | 199701329 A1 | 1/1997 |
| WO | 199706813 A1 | 2/1997 |
| WO | 199706842 A1 | 2/1997 |
| WO | 199712683 A1 | 4/1997 |
| WO | 1997012687 A1 | 4/1997 |
| WO | 199720590 A1 | 6/1997 |
| WO | 199723208 A1 | 7/1997 |
| WO | 199727804 A1 | 8/1997 |
| WO | 199735562 A1 | 10/1997 |
| WO | 199741833 A1 | 11/1997 |
| WO | 1998012511 A2 | 3/1998 |
| WO | 199827959 A2 | 7/1998 |
| WO | 199831346 A1 | 7/1998 |
| WO | 199839043 A1 | 9/1998 |
| WO | 1999001227 A1 | 1/1999 |
| WO | 1999007340 A1 | 2/1999 |
| WO | 1999011563 A1 | 3/1999 |
| WO | 1999016530 A1 | 4/1999 |
| WO | 1999043571 A1 | 9/1999 |
| WO | 199962495 A2 | 12/1999 |
| WO | 199965464 | 12/1999 |
| WO | 200001612 A2 | 1/2000 |
| WO | 200023037 A1 | 4/2000 |
| WO | 2000023065 A2 | 4/2000 |
| WO | 200027543 A1 | 5/2000 |
| WO | 200037336 A1 | 6/2000 |
| WO | 2000033965 A1 | 6/2000 |
| WO | 200049988 A2 | 8/2000 |
| WO | 200064779 A1 | 11/2000 |
| WO | 200113885 A1 | 3/2001 |
| WO | 200128489 A1 | 4/2001 |
| WO | 2001064182 A2 | 9/2001 |
| WO | 200187392 A2 | 11/2001 |
| WO | 2001085097 A2 | 11/2001 |
| WO | 200197888 A2 | 12/2001 |
| WO | 200198175 A1 | 12/2001 |
| WO | 200198176 A2 | 12/2001 |
| WO | 200204054 A1 | 1/2002 |
| WO | 200205879 A1 | 1/2002 |
| WO | 200217988 A2 | 3/2002 |
| WO | 200232899 A1 | 4/2002 |
| WO | 2002034411 A1 | 5/2002 |
| WO | 2002070141 A1 | 9/2002 |
| WO | 2002089887 A1 | 11/2002 |
| WO | 2003002045 A1 | 1/2003 |
| WO | 2003014832 A1 | 2/2003 |
| WO | 2003020253 A2 | 3/2003 |
| WO | 2003022332 A2 | 3/2003 |
| WO | 2003035030 A1 | 5/2003 |
| WO | 2003037159 A2 | 5/2003 |
| WO | 2003037259 A2 | 5/2003 |
| WO | 2003049786 A2 | 6/2003 |
| WO | 2003050031 A1 | 6/2003 |
| WO | 2003053350 A2 | 7/2003 |
| WO | 2003057593 A1 | 7/2003 |
| WO | 2003059547 A1 | 7/2003 |
| WO | 2003068299 A1 | 8/2003 |
| WO | 2003087097 A1 | 10/2003 |
| WO | 2003097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 200433954 A2 | 4/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2005000476 A1 | 1/2005 |
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 2005079997 A1 | 9/2005 |
| WO | 2005080001 A1 | 9/2005 |
| WO | 2005080002 A1 | 9/2005 |
| WO | 2005087299 A1 | 9/2005 |
| WO | 2005107837 A1 | 11/2005 |
| WO | 2005109948 A2 | 11/2005 |
| WO | 2005112892 A1 | 12/2005 |
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A2 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |
| WO | 2007049239 A2 | 5/2007 |
| WO | 2007060104 A2 | 5/2007 |
| WO | 2007060105 A1 | 5/2007 |
| WO | 2007060106 A1 | 5/2007 |
| WO | 2007060107 A1 | 5/2007 |
| WO | 2007060108 A2 | 5/2007 |
| WO | 2007062721 A1 | 6/2007 |
| WO | 2007090822 A2 | 8/2007 |
| WO | 2007101557 A2 | 9/2007 |
| WO | 2007128381 A1 | 11/2007 |
| WO | 2007134965 A1 | 11/2007 |
| WO | 2007134966 A1 | 11/2007 |
| WO | 2007134967 A1 | 11/2007 |
| WO | 2007134968 A1 | 11/2007 |
| WO | 2007141201 A1 | 12/2007 |
| WO | 2007141203 A1 | 12/2007 |
| WO | 2008023017 A2 | 2/2008 |
| WO | 2008047035 A2 | 4/2008 |
| WO | 2008077623 A1 | 7/2008 |
| WO | 2008124666 A2 | 10/2008 |
| WO | 2008138936 A2 | 11/2008 |

(56) References Cited

FOREIGN PATENT DOCUMENTS

| | | | |
|---|---|---|---|
| WO | 2008146025 A2 | 12/2008 |
| WO | 2009006137 A1 | 1/2009 |
| WO | 2009047021 A1 | 4/2009 |
| WO | 2009047173 A2 | 4/2009 |
| WO | 2009090245 A1 | 7/2009 |
| WO | 2009103510 A1 | 8/2009 |
| WO | 2009115200 A1 | 9/2009 |
| WO | 2010005946 A2 | 1/2010 |
| WO | 2010006870 A1 | 1/2010 |
| WO | 2010094305 A1 | 8/2010 |
| WO | 2010094413 A2 | 8/2010 |
| WO | 2010112358 A2 | 10/2010 |
| WO | 2010133294 A2 | 11/2010 |
| WO | 2011006711 A1 | 1/2011 |
| WO | 2011064160 A1 | 6/2011 |
| WO | 2011064163 A1 | 6/2011 |
| WO | 2011064164 A1 | 6/2011 |
| WO | 2011131779 A1 | 10/2011 |
| WO | 2011154295 A2 | 12/2011 |
| WO | 2011160932 A1 | 12/2011 |
| WO | 2012130757 A1 | 10/2012 |
| WO | 2012159914 A1 | 11/2012 |
| WO | 2012160047 A2 | 11/2012 |
| WO | 2012160052 A1 | 11/2012 |
| WO | 2012161685 A1 | 11/2012 |
| WO | 2012162305 A1 | 11/2012 |
| WO | 2013110601 A1 | 8/2013 |
| WO | 2013152861 A1 | 10/2013 |
| WO | 2013152894 A1 | 10/2013 |
| WO | 2015018901 A1 | 2/2015 |
| WO | 2015018903 A1 | 2/2015 |
| WO | 2015018904 A1 | 2/2015 |
| WO | 2015169431 A2 | 11/2015 |
| WO | 2015169732 A1 | 11/2015 |
| ZA | 199901520 A | 12/1999 |

OTHER PUBLICATIONS

"Lung Cancer". Merck Manual Home Edition, pp. 1-7. [Accessed at www.merck.com/mmhe/print/sec04/ch057/ch057a.html, on Jul. 28, 2010].
Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English of DE10007591, 2000.
Abstract in English of DE202006017793, 2007.
Abstract in English of FR2604363, Sep. 30, 1986.
Abstract in English of JPH0553470, 1993.
Abstract in English of JPH057246, 1993.
Abstract in English of JPH07118164, 1995.
Abstract in English of JPH07118166, 1995.
Abstract in English of JPH08277226,1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.
Ackermann et al.; Quantitative Online Detection of Low-Concentrated Drugs via a SERS Microfluidic System; ChemPhysChem; 2007; vol. 8; No. 18; pp. 2665-2670.
Beasley R et al: "Preservatives in Nebulizer solutions: Risks without Benefit" Pharmacotherapy, Boston, US, Bd. 18, Nr. 1, Jan. 1998.
Beasley R et al: "Preservatives in Nebulizer solutions: Risks without Benefit" Pharmacotherapy, Boston, US, Bd. 18, Nr. 1, Jan. 1998, pp. 130-139.

Bocci et al., "Pulmonary catabolism of interferons: alveolar absorption of 125I-labeled human interferon alpha is accompanied by partial loss of biological activity". Antiviral Research, vol. 4, 1984, pp. 211-220.
Chen, F-K et al., "A study of forming pressure in the tube-hydroforming process". Journal of Materials Processing Technology, 192-193, 2007, p. 404-409.
China Suppliers, Shanghai Lite Chemical Technology Co., Ltd. Product details on polyvinylpyrrolidones. Obtained online by the USPTO examiner on Apr. 24, 2011.
Cras et al., "Comparison of chemical cleaning methods of glass in preparation for silanization". Biosensors & Bioelectronics, vol. 14, 1999, pp. 683-688.
Diamond et al., "Substance P Fails to Mimic Vagally Mediated Nonadrenergic Bronchodilation". Peptides, vol. 3, 1982, pp. 27-29.
Elwenspoek et al., "Silicon Micromachining", Chapter 3, Mechanical Microsensors, Springer-Verlag Berlin Heidelberg, 2001, 4 pages.
English Language Abstract of EP1068906, 2001.
Fuchs et al., "Neopterin, biochemistry and clinical use as a marker for cellular immune reactions". International Archives of Allergy and Immunology, vol. 101, No. 1, 1993, pp. 1-6, Abstract 1p.
Han et al.; Surface activation of thin silicon oxides by wet cleaning and silanization; Thin Solid Films; 2006; vol. 510; No. 1-2; pp. 175-180.
Henkel et al.; Chip modules for generation and manipulation of fluid segments for micro serial flow processes; Chemical Engineering Journal; 2004; vol. 101; pp. 439-445.
Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic surfaces". Journal of Colloid and Interface Science, vol. 295, 2006, pp. 427-435.
Husseini et al., "Alkyl Monolayers on Silica Surfaces Prepared Using Neat, Heated Dimethylmonochlorosilanes with Low Vapor Pressures". Langmuir, vol. 19, 2003, pp. 5169-5171.
Ip et al., "Stability of Recombinant Consensus Interferon to Air-Jet and Ultrasonic Nebulization". Journal of Pharmaceutical Sciences, vol. 84, No. 10, Oct. 1995, pp. 1210-1214.
Jendle et al., "Intrapulmonary administration of insulin to healthy volunteers". Journal of Internal Medicine, vol. 240, 1996, pp. 93-98.
JP2005144459—English language abstract only.
Kutchoukov et al., "Fabrication of nanofluidic devices using glass-to-glass anodic bonding" Sensors and Actuators A, vol. 114, 2004, pp. 521-527.
Lougheed et al., "Insulin Aggregation in Artificial Delivery Systems". Diabetologia, vol. 19, 1980, pp. 1-9.
Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).
Niven et al., "Some Factors Associated with the Ultrasonic Nebulization of Proteins". Pharmaceutical Research, vol. 12, No. 1, 1995, pp. 53-59.
Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J., Chapter 95, R97-1185.
Trasch et al., "Performance data of refloquant Glucose in the Evaluation of Reflotron". Clinical Chemistry, vol. 30, 1984, p. 969 (abstract only).
Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.
Wang et al.; Self-Assembled Silane Monolayers: Fabrication with Nanoscale Uniformity; Langmuir; 2005; vol. 21; No. 5; pp. 1848-1857.
International Search Report and Written Opinion for PCT/EP2015/000903 dated Nov. 5, 2015.

NEBULIZER

BACKGROUND

The present invention relates to a nebulizer and to a container.

WO 2012/162305 A1 discloses a nebulizer. A container can be inserted into a housing of the nebulizer. The housing is closed by a lower housing part. By rotating the housing part the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual pressing a button, the drive spring is released and moves the delivery tube into the pressure chamber so that the fluid is put under pressure by the drive spring and is delivered or atomized through a nozzle into a mouthpiece as an aerosol, without the use of propellant gas. Thus, the container is moving axially forth and back during conveying of the fluid to be nebulized, and during pressure generation and nebulization.

The container may be connected inseparably with the housing part by a securing device forming a transportation lock for holding the container unmovable in a delivery state.

The nebulizer comprises an indicator device for counting and/or indicating a number of uses performed or still possible. The indicator device blocks further use in a locked state when a predetermined number of uses has been reached or exceeded with the current container. Then, the container can be replaced together with a housing part and the nebulizer can be used further with the new container.

U.S. Pat. No. 7,823,584 B2 discloses a similar nebulizer, wherein a counter device can be integrated into a housing part that is exchangeable or replaceable together with the container, which is inseparable from the housing part.

WO 2007/104694 A1 discloses an inhaler for powdery substances with an indicator device which may comprise a worm gear for driving an indicator element.

SUMMARY OF THE INVENTION

Object of the present invention is to provide a nebulizer and a container for a nebulizer allowing easy and/or secure operation and handling and/or a compact and/or reliable construction, preferably while allowing replacement of the container without replacement of any housing part of the nebulizer.

The above object is achieved by a nebulizer as described herein or by a container as described herein.

The present invention relates to a nebulizer for nebulizing a fluid, preferably liquid medicament, from a preferably replaceable container containing the fluid, and relates to the container. An indicator device is provided for counting and/or indicating the number of uses already performed or still possible with the container.

In particular, the indicator device or an associated locking device can lock the container and/or nebulizer or can cause the locking of the container and/or nebulizer against further use in a locked state when a predetermined number of uses has been reached or exceeded with the respective container.

Preferably, the nebulizer comprises a housing part which can be detached from the nebulizer or opened for replacing the container.

According to one aspect of the present invention, the indicator device is preferably adapted to at least partially open or to cause at least partial opening of the nebulizer and/or housing part in the locked state and/or when the locked state is reached and/or the indicator device is adapted to prevent the complete closure of the nebulizer and/or housing part in the locked state. In particular, this allows a very compact and simple construction and/or secure operation. Preferably, the number of necessary parts and components can be minimized. In particular, this supports an intuitive handling.

According to a further aspect of the present invention, the indicator device blocks complete assembly of the container with the nebulizer or with the nebulizer housing and/or housing part in the locked state. In particular, this allows a very compact and simple construction and/or secure operation. Preferably, the number of necessary parts and components can be minimized. In particular, this supports an intuitive handling.

According to another aspect of the present invention, the indicator device is preferably adapted to block complete inserting of the container into the nebulizer and/or housing part in the locked state. This allows a very compact and simple construction and/or secure operation. Preferably, this supports an intuitive handling. Preferably, this prevents re-use or re-insertion of an already used container and, thus, allows a very simple and secure construction.

According to a further aspect of the present invention, the indicator device is preferably adapted to block full axial or stroke-like movability of the container within in the nebulizer in the locked state. This allows very compact and simple construction. Preferably, the number of necessary parts and components can be minimized. Further, this allows secure operation.

Preferably the nebulizer and/or container cannot be used anymore in the locked state when the indicator device has detected that a predetermined number of uses has been reached or exceeded, in particular with the respective container.

The indicator device may either directly or indirectly lock or initiate or trigger locking of the nebulizer and/or container against further use. In particular, the indicator device may directly actuate the locking device or indirectly initiate actuation of the locking device. Preferably, the indirect actuation is realized by means or via at least partial opening of the nebulizer or its housing or housing part in order to lock the nebulizer against further use with the current container.

Preferably, the nebulizer is blocked (automatically) against further use or tensioning if the nebulizer housing or housing part is at least partially open or opened or if, with other words, when the nebulizer or its housing is not (completely) closed.

It is also possible that the nebulizer is not immediately blocked against further use when the indicator device enters the locked state. Instead, the indicator device may initiate or cause or trigger in its locked state that the locking device is going to block the nebulizer against further use, e.g. during the next actuation or tensioning or the like. Thus, the locking device may enter its locking state later, e.g. after at least partial opening of the nebulizer and/or at least partial tensioning of the nebulizer or rotation of the housing part or inner part of the nebulizer or the like.

Therefore, the blocking of the nebulizer can be initiated or caused by the indicator device not only indirectly, but alternatively or additionally also later during further handling, operation, actuation or the like. In the latter case, the indicator device blocks or initiates or causes blocking of the nebulizer and/or container against further use also preferably in the sense of the present invention.

Preferably, the locking of the nebulizer against further use can be overcome by replacing the container, in particular including the indicator device, against one not yet used.

According to another aspect of the present invention, the indicator device is preferably inseparably connected with the container or with a container housing of the container, but separable from the nebulizer or its housing and from the housing part, so that the indicator device is replaceable together with the container. This allows reuse of the nebulizer and the housing part with another container including another indicator device. Thus the overall size of the components to be exchanged is kept small, so that the replacement packages are size reduced, so that transport of a large number of packages is facilitated.

Preferably, the indicator device is fixedly arranged at a bottom of the container and/or opposite to an outlet of the container. This allows a very compact construction. Further, the indicator device does not interfere with the fluidic connection of the container to the nebulizer or vice versa.

According to a further aspect of the present invention, the indicator device comprises preferably a piercing element for opening and an aeration opening. In particular, this allows a very compact construction and/or supports secure operation.

Preferably, the indicator device comprises an indicator element and an actuation element for indexing the indicator element. In particular, the indicator element displays an indication of the number of uses already performed or still possible with the respective container.

Preferably, a linear movement of the actuation element causes a rotational movement of the indicator element.

Even more preferably, the actuation element is set in motion by a relative longitudinal movement between the container with the indicator device and the housing and/or housing part of the nebulizer.

According to another aspect of the present invention, the actuation element in the indicator device is preferably constructed to also block further use of the container in the locked state. In particular, this allows a very compact and simple construction and/or secure operation. Preferably, the number of necessary parts and components can be minimized.

According to a further aspect of the present invention, the actuation element is preferably moveable back and forth between a first and second position for indexing the indicator element and is moveable—at least or only once—into a third position to block further use of the container in the locked state. In particular, this allows a very compact and simple construction and/or secure operation. Preferably, the number of necessary parts and components can be minimized.

According to another aspect of the present invention, the actuation element is preferably moveable transversally to a longitudinal or dispensing direction of the container or nebulizer. In particular, this allows a very compact and simple construction and/or secure operation. Preferably, the number of necessary parts and components can be minimized.

Preferably, the indicator device comprises a blocking part which blocks further use of the container and/or nebulizer in the locked state.

According to another aspect of the present invention, the blocking part is preferably formed by or made integral with the actuation element. In particular, this allows a very compact and simple construction and/or secure operation. Preferably, the number of necessary parts and components can be minimized.

According to another aspect of the present invention, the blocking part is preferably integrated into a housing of the indicator device. In particular, this allows a very compact and simple construction and/or secure operation. Preferably, the number of necessary parts and components can be minimized.

According to a further aspect of the present invention, the blocking part is preferably moveable transversally to a longitudinal or dispensing direction of the container or nebulizer. In particular, this allows a very compact and simple construction and/or secure operation. Preferably, the number of necessary parts and components can be minimized.

According to a further aspect of the present invention, the blocking part preferably closes an insertion opening of the indicator housing in the locked state. In particular, in the unlocked state, the insertion opening is for receiving a driving part attached to the housing or the housing part of the nebulizer, so that upon a relative movement between the indicator housing and/or the container and the nebulizer housing, the driving part actuates the indicator device in particular such that a use of the nebulizer is counted and/or indicated in the indicator device. In particular, this allows a very compact and simple construction and/or secure operation. Preferably, the number of necessary parts and components can be minimized.

According to another or further aspect of the present invention, the blocking part preferably actuates a locking device or its locking element of the nebulizer in the locked state. This actuation can be realized directly by respective cooperation of the blocking part if the locking device or its locking element or, alternatively, indirectly, in particular by opening the nebulizer or closing an insertion opening of the indicator device or the like which results in an actuation of the locking device or its locking element. Thus, further use, in particular further dispensing or nebulization of fluid can be prevented or blocked in the locked state.

The above aspects of the present invention and the further aspects described below can be realized independently from each other, and in any combination.

BRIEF DESCRIPTION OF THE DRAWING

Further advantages, features, characteristics and aspects of the present invention will become apparent from the claims and the following description of a preferred embodiment with reference to the drawings. It shows:

FIG. 1 a schematic section of a known nebulizer in a non-tensioned state;

FIG. 2 a schematic section, rotated 90° compared with FIG. 1, of the known nebulizer in a tensioned state;

FIG. 3 a schematic section of a nebulizer with an inserted container in a non-tensioned state according to a preferred embodiment of the present invention;

FIG. 4 a partial enlargement of the encircled part of FIG. 3;

FIG. 5 a perspective view of the section of the nebulizer according to FIG. 3;

FIG. 6 an enlargement of the encircled part of FIG. 5;

FIG. 7 a schematic exploded view of an indicator device according to a preferred embodiment of the present invention;

FIG. 8 an axial section of the indicator device in an actuated state;

FIG. 9 an axial section of the indicator device in a locked state;

FIG. 10 a perspective section of the indicator device in an actuated state;

FIG. 11 a perspective section of the indicator device in an released state;

FIG. 12 a partial enlargement of the nebulizer similar to FIG. 4, but in a partially tensioned state;

FIG. 13 a partial enlargement of the nebulizer similar to FIG. 4, but in a fully tensioned state;

FIG. 14 a partial section of the nebulizer similar to FIG. 4, but in an intermediate state during a dispensing stroke;

FIG. 15 a partial section of the nebulizer similar to FIG. 4, but with an indicator device of the container in a locked state;

FIG. 16 a schematic section of the nebulizer in the locked state after next tensioning with partially opened housing part and with locked locking device;

FIG. 17 a partial enlargement of the encircled part of FIG. 13;

FIG. 18 a schematic section of the nebulizer similar to FIG. 3 with unlocked locking device;

FIG. 19 a schematic section of the indicator device in the initial state according to a modified embodiment; and FIG. 20 a perspective section of the indicator device according to FIG. 19.

DESCRIPTION OF THE PREFERRED EMBODIMENTS

In the Figures, the same reference numerals are used for identical or similar parts, resulting preferably in corresponding or comparable properties and advantages, even if the associated description is not repeated.

FIGS. 1 and 2 show a known nebulizer 1 for atomizing a fluid 2, particularly a highly effective pharmaceutical composition, medicament or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed or dispensed, which can be breathed in or inhaled by a user. Usually the inhaling is done at least once a day, more particularly several times a day, preferably at set intervals, depending on the complain or illness from which a patient is suffering.

The nebulizer 1 is provided with or comprises an insertable or replaceable container 3 containing the fluid 2. The container 3 thus forms a reservoir for the fluid 2, which is to be nebulized. Preferably, the container 3 contains multiple doses of fluid 2 or active substance in particular sufficient to provide up to 200 dosage units or doses, for example, i.e. to allow up to 200 sprays or applications. A typical container 3, as disclosed in WO 96/06011 A1, holds e.g. a volume of about 2 to 20 ml.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the container 3 can be replaced or exchanged, wherein the total number of uses of the nebulizer 1 and thus the number of containers 3, which can be used with the same nebulizer 1, is preferably restricted, e.g. to a total number of four or five containers 3. WO 2012/162305 A1 discloses additionally such a restriction to the total numbers of containers 3 which can be used with the same nebulizer 1.

The container 3 is preferably substantially cylindrical or cartridge-shaped and once the nebulizer 1 has been opened the container 3 can be inserted therein preferably from below and changed if desired. It is preferably of rigid construction, the fluid 2 in particular being held in a collapsible bag 4 in the container 3. In particular, the container 3 comprises a venting opening or hole 23 which is opened before or during first use.

The nebulizer 1 comprises a delivery mechanism, preferably a pressure generator 5, for conveying and nebulizing the fluid 2, particularly in a preset and optionally in an adjustable dosage amount.

The nebulizer 1 or pressure generator 5 comprises preferably a holder 6 for releasable holding of the container 3, a drive spring 7 associated to the holder 6, only partly shown, and/or a blocking element 8 preferably in form of or with a button for preferably manual actuation or depressing. The blocking element 8 can catch and block the holder 6 and can be manually operated to release the holder 6 allowing drive spring 7 to expand.

The nebulizer 1 or pressure generator 5 comprises preferably a conveying element, such as a conveying tube 9, a non-return valve 10, a pressure chamber 11 and/or an nozzle 12 for nebulizing the fluid 2 into a mouthpiece 13.

The completely inserted container 3 is fixed or held in the nebulizer 1 via the holder 6 such that the conveying element fluidically connects the container 3 to the nebulizer 1 or pressure generator 5. Preferably, the conveying tube 9 penetrates into the container 3.

The nebulizer 1 or holder 6 is preferably constructed so that the container 3 can be exchanged.

When the drive spring 7 is axially tensioned in the tensioning process, the holder 6 with the container 3 and the conveying tube 9 are moved downwards in the drawings and fluid 2 is sucked out of the container 3 into the pressure chamber 11 of the pressure generator 5 through the non-return valve 10. In this state, the holder 6 is caught by the blocking element 8 so that the drive spring 7 is kept compressed. Then, the nebulizer 1 is in the tensioned state.

During the subsequent relaxation in the nebulization process after actuation or pressing of the blocking element 8 the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1, and, thus, dispensed.

Generally, the nebulizer 1 operates with a spring pressure of 5 to 200 MPa, preferably 10 to 100 MPa on the fluid 2, and/or with a volume of fluid 2 delivered per stroke of 10 to 50 µl, preferably 10 to 20 µl, most preferably about 15 µl. The fluid 2 is converted into or nebulized as aerosol 14, the droplets of which have an aerodynamic diameter of up to 20 µm, preferably 3 to 10 µm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

The nebulizer 1 comprises preferably a housing 24 and/or (upper) housing part 16 and optionally a biasing or inner part 17 preferably which is rotatable relative thereto (FIG. 2) and/or has an upper part 17a and a lower part 17b (FIG. 1).

The nebulizer 1 or housing 24 comprises preferably a (lower) housing part 18. This part 18 is in particular manually operable, and/or releasable fixed, particularly fitted or held onto the inner part 17, preferably by means of a retaining element 19.

Preferably, the housing parts 16 and 18 and/or other parts form the housing 24 of the nebulizer 1.

In order to insert and/or replace the container 3, preferably the housing 24 can be opened and/or the housing part 18 can be detached from the nebulizer 1, inner part 17 or housing 24.

Generally and preferably, the container 3 can be inserted before the housing 24 is closed and/or before the housing part 18 is connected to the housing 24. The container 3 may be inserted, opened and/or fluidically connected to the delivery mechanism automatically or simultaneously when (completely) connecting the housing part 18 to the housing 24/nebulizer 1 and/or when (completely) closing the housing 24/nebulizer 1. Preferably, the container 3 is open or fluidically connected when tensioning the nebulizer 1 for the first time with the current container 3.

Preferably, the nebulizer 1 or drive spring 7 can be manually activated or tensioned or loaded, in particular by actuation of an actuation member, here preferably by rotating housing part 18 or any other component.

The actuation member, preferably the housing part 18, can be actuated, here rotated relative to the upper housing part 16, carrying with it or driving the inner part 17. The inner part 17 acts on a gear or transmission to transform the rotation in an axial movement. As a result the drive spring 7 is tensioned in the axial direction by means of the gear or transmission (not shown) formed between the inner part 17, in particular its upper part 17a, and the holder 6 and acting on the holder 6. During tensioning the container 3 is moved axially downwards until the container 3 assumes an end position as shown in FIG. 2. In this activated or tensioned state the drive spring 7 is under tension and can be caught or held by the blocking element 8. During the nebulizing process the container 3 is moved back into its original position (non-tensioned position or state shown in FIG. 1) by (the force of) the drive spring 7. Thus the container 3 executes a lifting or stroke movement during the tensioning process and during the nebulizing process.

The housing part 18 preferably forms a cap-like lower housing part and/or fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal or foil 50 thereon with a piercing element 22 when the container 3 makes contact with it for the first time, to allow air in or aeration, preferably by opening or piercing venting hole 23. The venting hole 23 allows for pressure compensation inside the container 3 when fluid 2 is drawn from the container 3 during the actuation of the nebulizer 1.

The nebulizer 1 comprises preferably an indicator device 25, which counts in particular actuations of the nebulizer 1, preferably by detecting its tensioning or the rotation of the inner part 17 relative to the upper part 16 or housing 24. Preferably, the counter device 25 or an associated locking device 26 locks the nebulizer 1 against (further) actuation or use, e.g. blocks further rotation of the housing part 18/inner part 17 and, thus, tensioning of the nebulizer 1 or its drive spring 7 and/or blocks actuation of the blocking element 8, in a locked state when a certain number of actuations or operations or discharged doses has been reached or exceeded.

In the following and with reference to the further figures, a preferred embodiment of the nebulizer 1, container 3, indicator device 25 and/or locking device 26 is described and shown according to the invention, wherein primarily important aspects and differences will be described and the previous aspects, features and explanations apply preferably additionally or correspondingly even without repetition.

FIG. 3 shows the nebulizer 1 with the container 3 and indicator device 25 according the present invention in a schematic section (longitudinal section) in the non-tensioned state with completely closed nebulizer housing 24 and, thus, closed housing part 18, wherein the container 3 including the proposed indicator device 25 are inserted into or received within the nebulizer 1 and/or housing 24.

FIG. 4 shows an enlarged partial section of the encircled part of FIG. 3. FIG. 5 shows a perspective view of the section of the nebulizer 1 of FIG. 3. FIG. 6 shows a partial enlargement of the encircled part of FIG. 5.

The nebulizer 1 has preferably a longitudinal form or axis which corresponds to the axial direction and/or to the main dispensing direction and/or to stroke movement of the container 3 during tensioning and dispensing.

In the shown non-tensioned state, the nebulizer 1 or its mouthpiece 13 is preferably closed by a mouthpiece cover 27. The mouthpiece cover 27 is preferably pivotable to allow opening of the mouthpiece 13 for using the nebulizer 1.

Preferably, the indicator device 25 is directly and/or secured without possibility of release or fixed to or connected with the container 3. In particular, the indicator device 25 is associated to a respective container 3. If the container 3 of the nebulizer 1 is replaced, the indicator device 25 is necessarily or positively replaced as well.

Preferably, the indicator device 25 is fixedly arranged at the bottom or container base 21 of the container 3 and/or opposite to an outlet or head 28 of the container 3.

In the present embodiment, the indicator device 25 is preferably directly connected to or abuts at an outer case or preferably rigid housing 29 of the container 3.

Preferably, the indicator device 25 and the container 3 are connected by form-fit and/or snap-fit.

In particular, the indicator device 25 circumvents and/or grips over a (lower or bottom) edge 30 and/or any other protrusion or the like of the container 3. In the present embodiment, the edge 30 is a little bit wider in diameter so that it protrudes radially over the essentially cylindrical outer form of the side wall of the container 3/container housing 29.

The diameter of the indicator device 25 is preferably at least essentially equal to or slightly greater than the diameter of the container 3 or its edge 30.

The edge 30 is preferably formed between the side wall and the bottom or base 21 of the container 3 or container housing 29.

The indicator device 25 comprises a housing 31 and/or preferably has an at least essentially cylindrical form.

The indicator device 25 or its housing 31 is preferably attached to the container 3 or its base 21 or housing 29 with an at least essentially flat and/or axial side.

The indicator device 25 or its housing 31 comprises preferably a holding or gripping section 32 for connecting the indicator device with the container 3. Preferably, the gripping section 32 circumvents the edge 30 and/or grips around or over the edge 30.

In the present embodiments, the gripping section 32 is preferably annular and/or grips over the edge 31 at positions distributed over the circumference of the edge 30 or container 3.

Preferably, the indicator device 25 and the container 3 are connected with each other by a snap-fit or click connection. Preferably, the container 3 and the indicator device 25 are connected with each other by axially snapping one part on the other.

Preferably, the gripping section 32 is sufficiently elastic in radial direction so that the container 3 can be entered axially with its edge 30. In the present embodiment, the gripping section 32 preferably comprises a respectively inclined insertion face to facilitate insertion of edge 30 into the annular gripping section 32 or between circumferentially distributed gripping sections 32.

It has to be noted that other constructional solutions are possible for connecting the container 3 or its housing 29 with the indicator device 25 or its housing 31 or vice versa. In particular, the two parts can be connected with each other additionally or alternatively by welding, brazing, gluing, screwing, clamping, hot-pressing, or the like.

FIG. 7 shows in a schematic, exploded view the indicator device 25 according to the preferred embodiment of the present invention.

The indicator or its housing 31 comprises preferably an upper part 33 and a lower part 34.

Preferably, the upper part 33 holds or forms the gripping section 32.

The indicator device 25 comprises preferably an indicator element 35 and an associated actuation element 36 and/or a transmission 40 or gear 41 for indexing the indicator element 35 or for causing the indexing of the indicator element 35.

The indicator device 25 is for counting and/or indicating a number of uses performed or still possible with the respective or associated container 3. Preferably, the indicator element 35 comprises markings 37, such as one or more symbols, numbers, colored or shaded areas or the like, for at least roughly indicating the number of uses already performed with or still possible with the respective container 3. In the present embodiment, the indicator element 35 is preferably rotatable and/or comprises a circumferential wall or outer surface with the at least one marking 37.

The indicator housing 31 comprises preferably a window 31a, in particular in the circumferential wall through the relevant marking 37 is visible for a user or patient, preferably through the housing part 18 which is in particular transparent.

The actuation element 36 comprises preferably an actuation arm 38 which, intern comprises preferably a free or actuation end 39, for direct or indirect actuation or indexing of the indicator element 35. Indexing means that the indicator element 35 is moved forward in increments or steps.

Preferred is an indirect actuation or driving so that the actuation element 36 or its arm 38 actuates or drives the indicator element 35 via a transmission 40. In the present embodiment, the transmission 40 results in a reduction and/or is realized as a worm device.

The indicator device 25 or transmission 40 comprises preferably a gear 41 and/or a worm 42. Most preferably, the worm 42 is directly formed by the gear 41 so that the gear 41 forms a worm gear and preferably comprises radially protruding teeth 43 in which at least one convolution of the won't 42 is formed (compare the horizontal or axial sections of the mounted indicator device 25 shown in FIGS. 8 and 9).

The gear 41 comprises preferably an axle, in particular one or more axle sections 44 which may axially protrude on opposite sides as realized in the present embodiment.

The actuation element 36 causes a rotation of the gear 41 around an axis preferably perpendicular to the direction of movement of the actuation element 36, the axis preferably being arranged in a horizontal plane identical or parallel to the plane given by the movement of the actuation element 36.

The gear 41 is rotatably held preferably by the housing 31 or lower housing part 34, preferably by two bearing sections 45 of the lower part 34. Preferably, the bearing sections 45 comprise recesses for rotatably holding the axle sections 44. However, other constructional solutions are possible as well.

The housing 31 or lower part 34 bears preferably the indicator element 35 such that it can rotate. In the present embodiment, the lower part 34 comprises preferably two bearing portions 46 arranged on opposite radial sides and axially protruding for rotatably bearing the indicator element 35. The actuation element 35 and/or transmission 40 are preferably arranged at least essentially in between the bearing portions 46.

The indicator device 25 comprises preferably an actuation spring 47, in particular for biasing the actuation element 36 into a preferred direction and/or for driving the indicator element 35.

Figure 8:
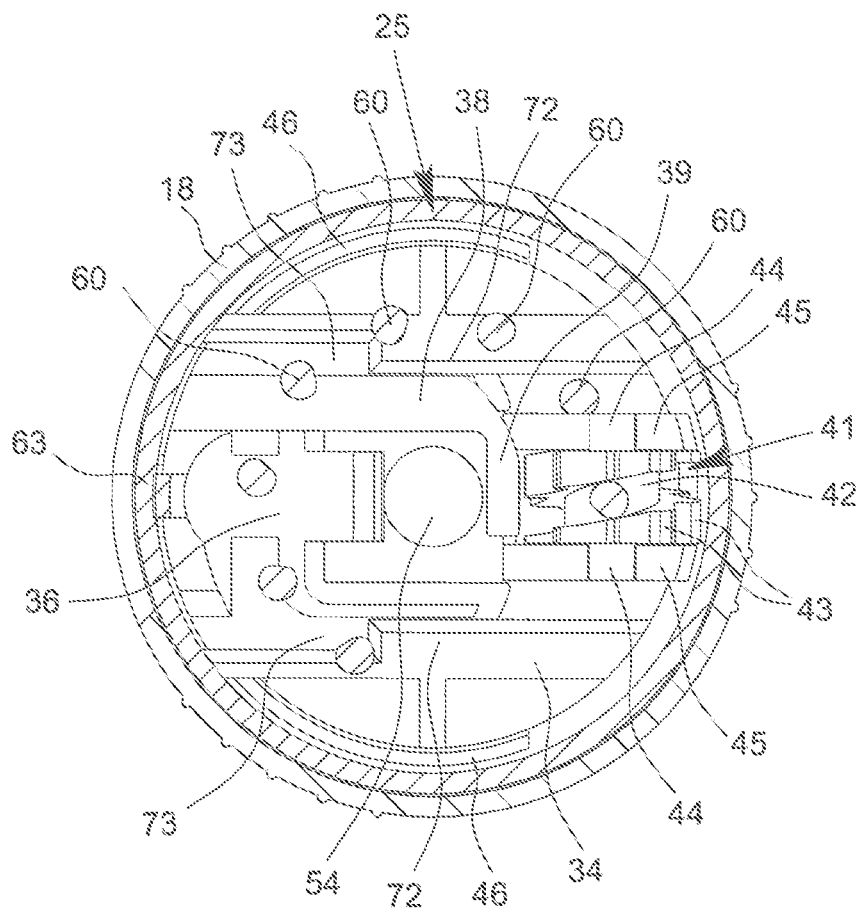
FIG. 8 shows in a horizontal or axial section the mounted indicator device 25 in an actuated state where the actuation element 36 has been moved or pushed sideward, namely starting from the first position shown in FIGS. 3 to 6 towards the left into a second position which is shown in FIG. 8.
Figure 9:
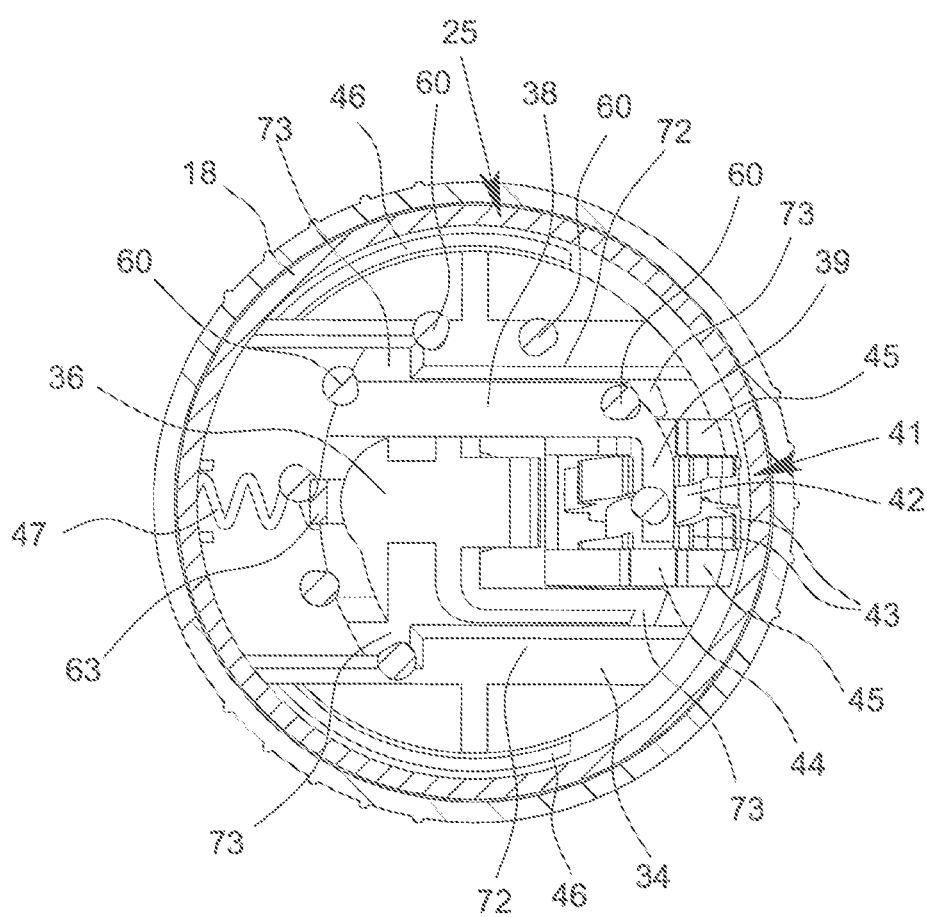
FIG. 9 shows in a similar section as FIG. 8 the indicator device 25 in a locked state where the actuation element 36 is in a locked, third position.

It can been seen from FIGS. 8 and 9 that protrusions 60 of the indicator element 35 (not shown in FIGS. 8 and 9) extend axially, wherein always at least one protrusion 60 is caught in the worm 42 so that a worm drive is formed between the gear 41 and the indicator element 35. Thus, any rotation of gear 41 is transformed in a reduced rotation of the indicator element 35. Further, a permanent engagement between the gear 41 and the indicator element 35, more precisely between at least one protrusion 60 and the worm 42, is ensured. However, other constructional solutions or couplings between the gear 41 and the indicator element 35 are possible.

Figure 10:
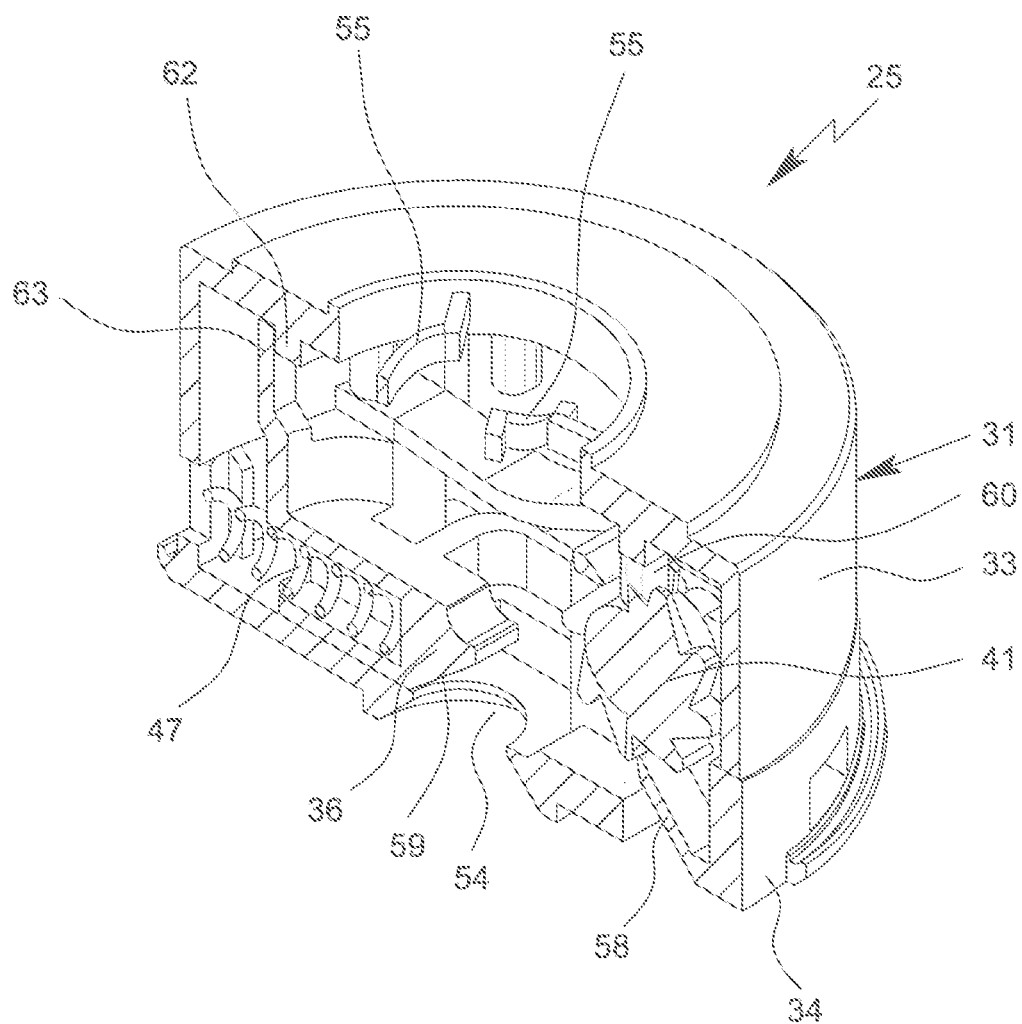
Figure 11:
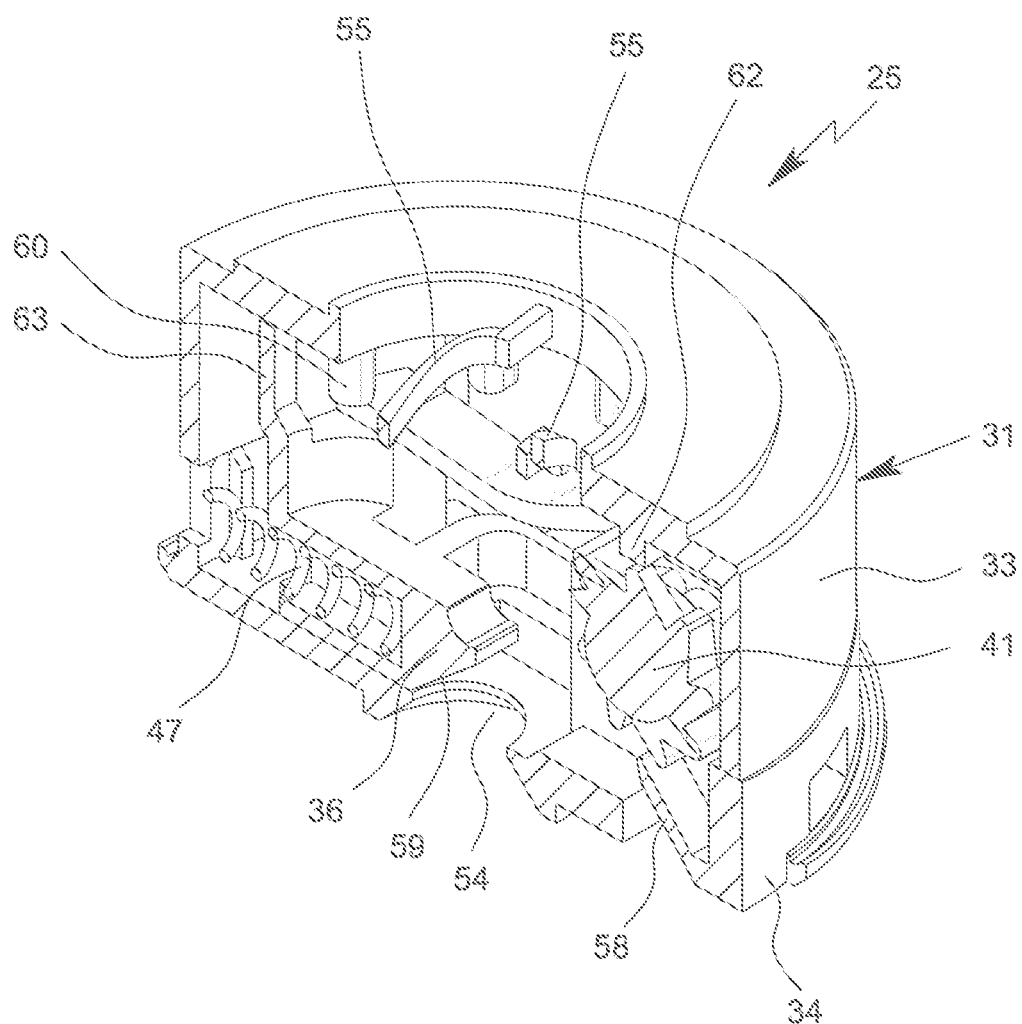

FIG. 10 shows the mounted indicator device 25 in a perspective section in the initial, first position and state. FIG. 11 shows the indicator device 25 in a similar perspective section, but with released actuation element 36, i.e. just before the locked state is reached.

Preferably, the transmission 40 or gear 41 forms a worm (helical groove) 42 with at least one convolution, preferably a with about 1.5 or more convolutions, so that always at least one engaging element of the indicator element 35 or of any other transmission component, in particular the inwardly or axially projecting protrusion 60, engages in the worm 42. Thus, rotation of the gear 41 around its preferably transversal axis results in a rotation of the indicator element 35 around its preferably longitudinally oriented rotation axis. However, other constructional solutions are possible as well.

Preferably, the teeth 43 are relatively long and/or extend radially sufficiently so that the protrusions are securely guided within the convolutions of the worm 42, in between the teeth 43, and that the actuation portion 39 can still move in radial direction between the protrusion 60 engaging into the worm 42 and the gear 41 in order to actuate or rotate the gear 41 in the desired manner. For this purpose, the actuation portion 39 may engage into respectively deep cut outs between the teeth 43 in order to be able to move below the respective projection 60.

The indicator device 25 comprises preferably a piercing part 48 (compare FIGS. 3 to 6).

The piercing part 48 is arranged within the indicator device 25 or its housing 31.

The piercing part 48 is preferably axially moveable.

The piercing part 48 is preferably moveable such that it can protrude towards the container 3 and/or can open an aeration opening, preferably the venting hole 23, of the container 3, in particular by breaking or piercing a foil 50 covering the venting hole 23.

In the present embodiment, the piecing element 48 comprises preferably an opening end or tip 49 which can open or pierce the foil 50 covering the container base 21, in particular an indention 51 formed in the container 3 or its base 21. Preferably, the indention 51 comprises a break through which forms the venting hole 23. However, other constructional solutions are possible as well.

Figure 4:
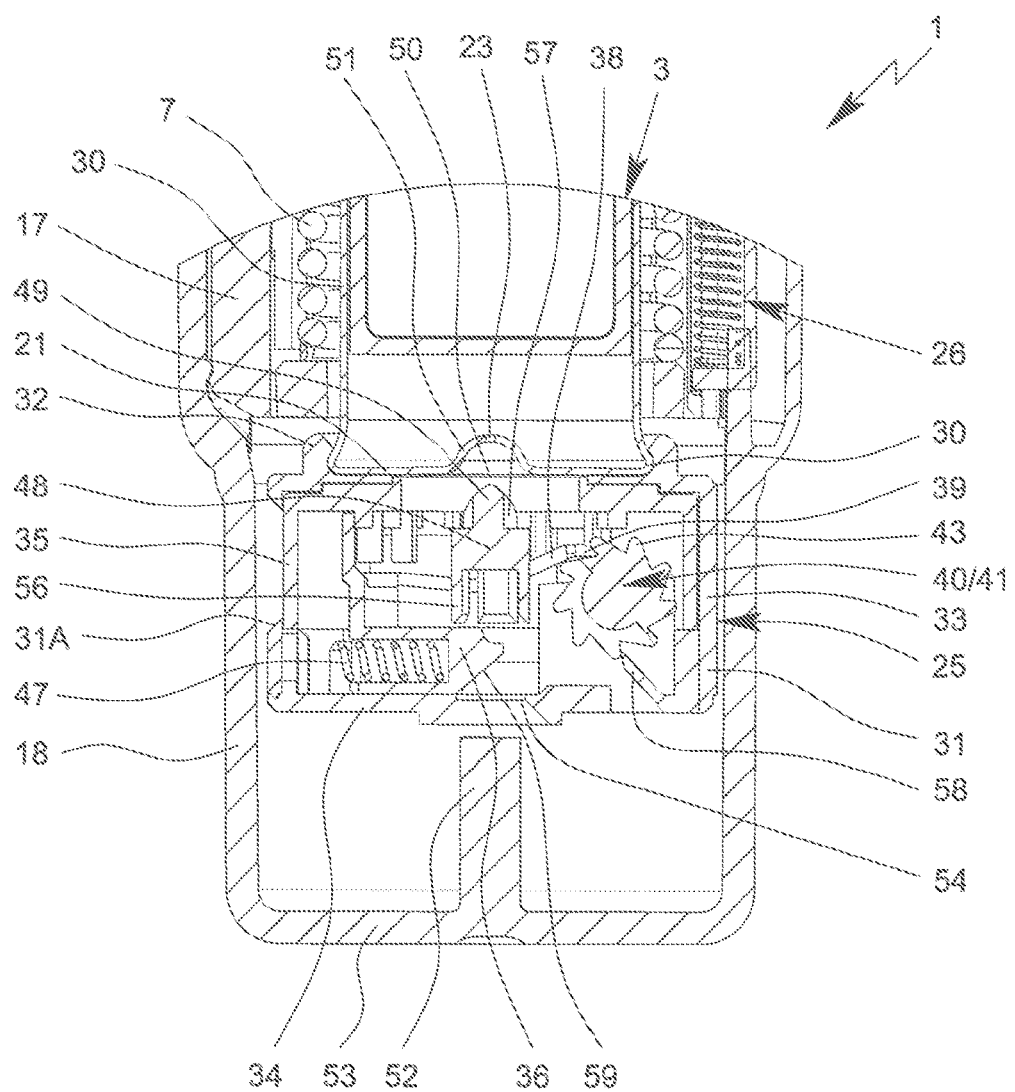
Figure 5:
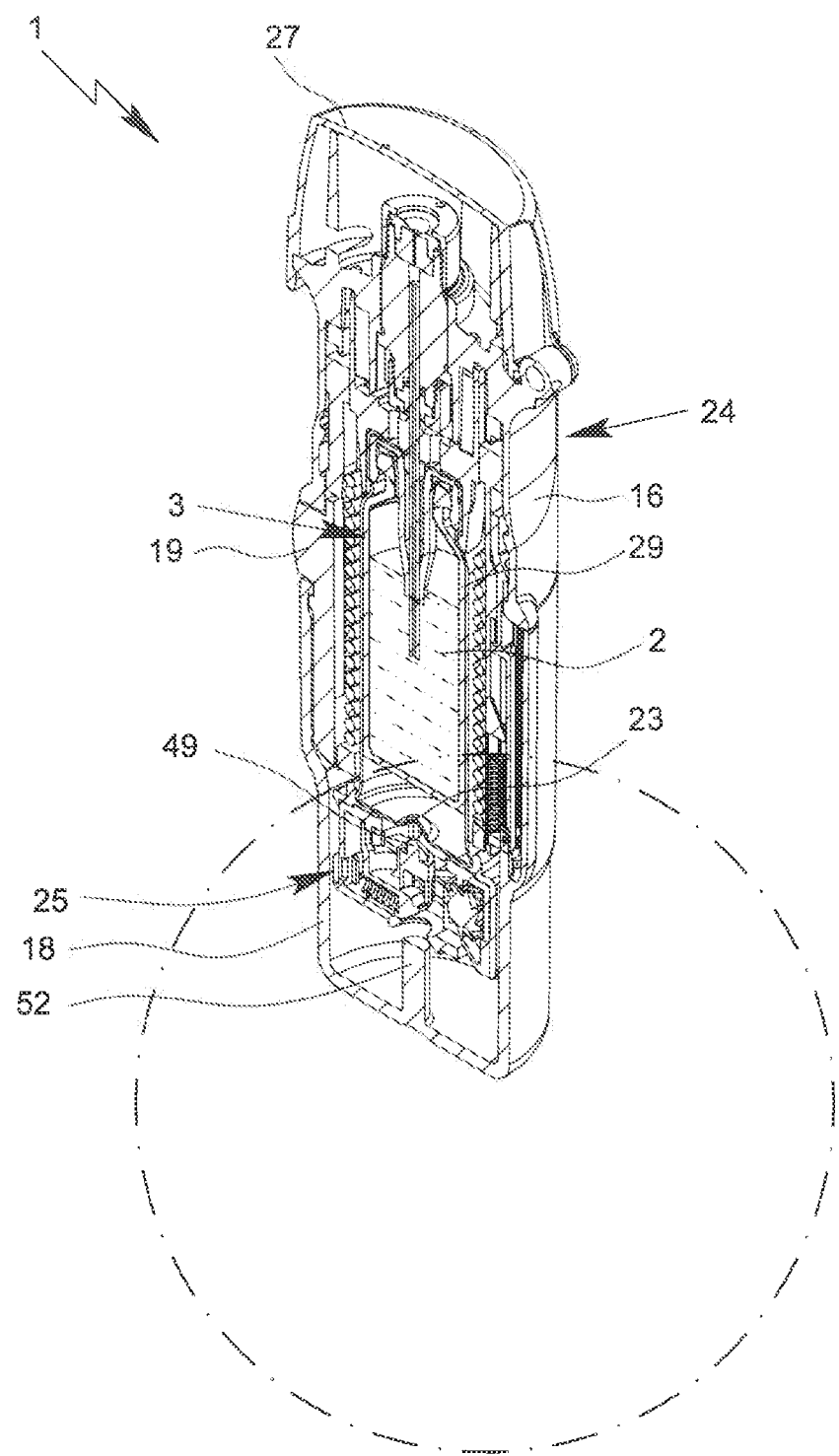
Figure 6:
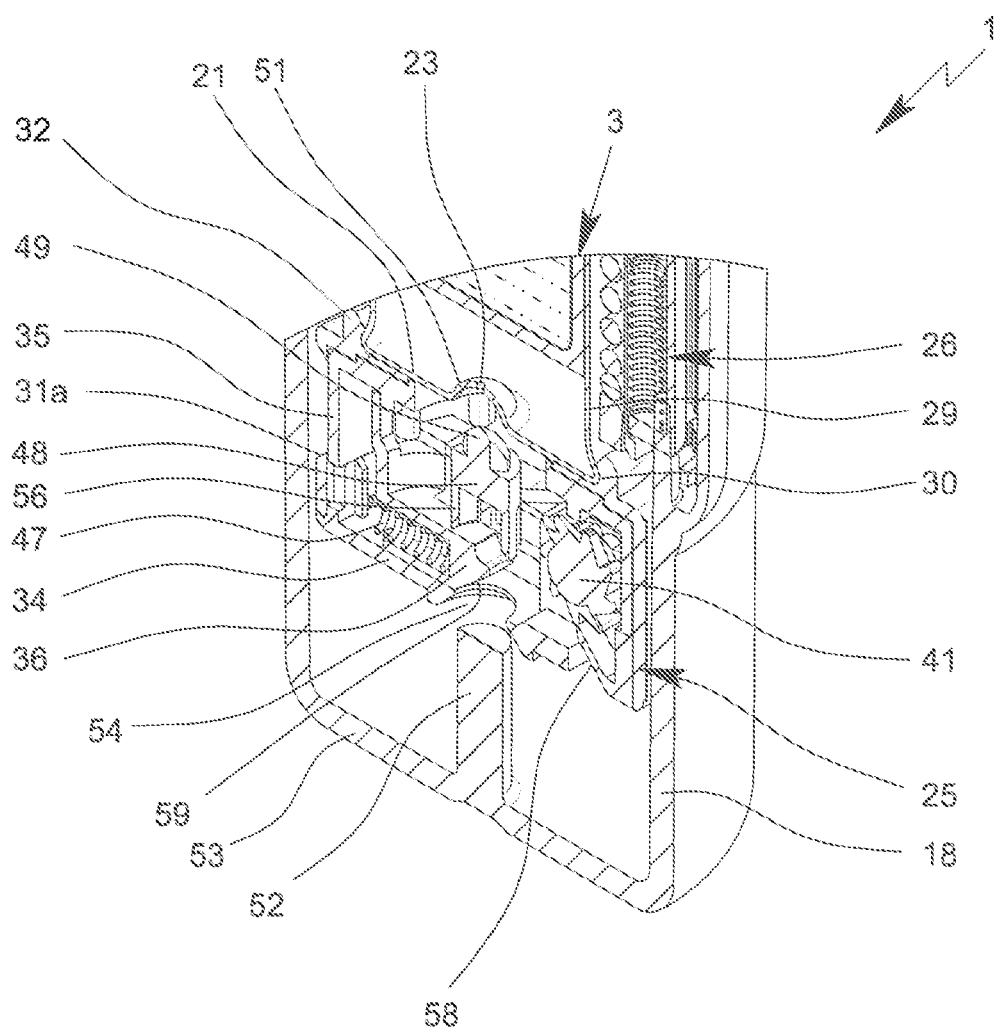
Figure 7:
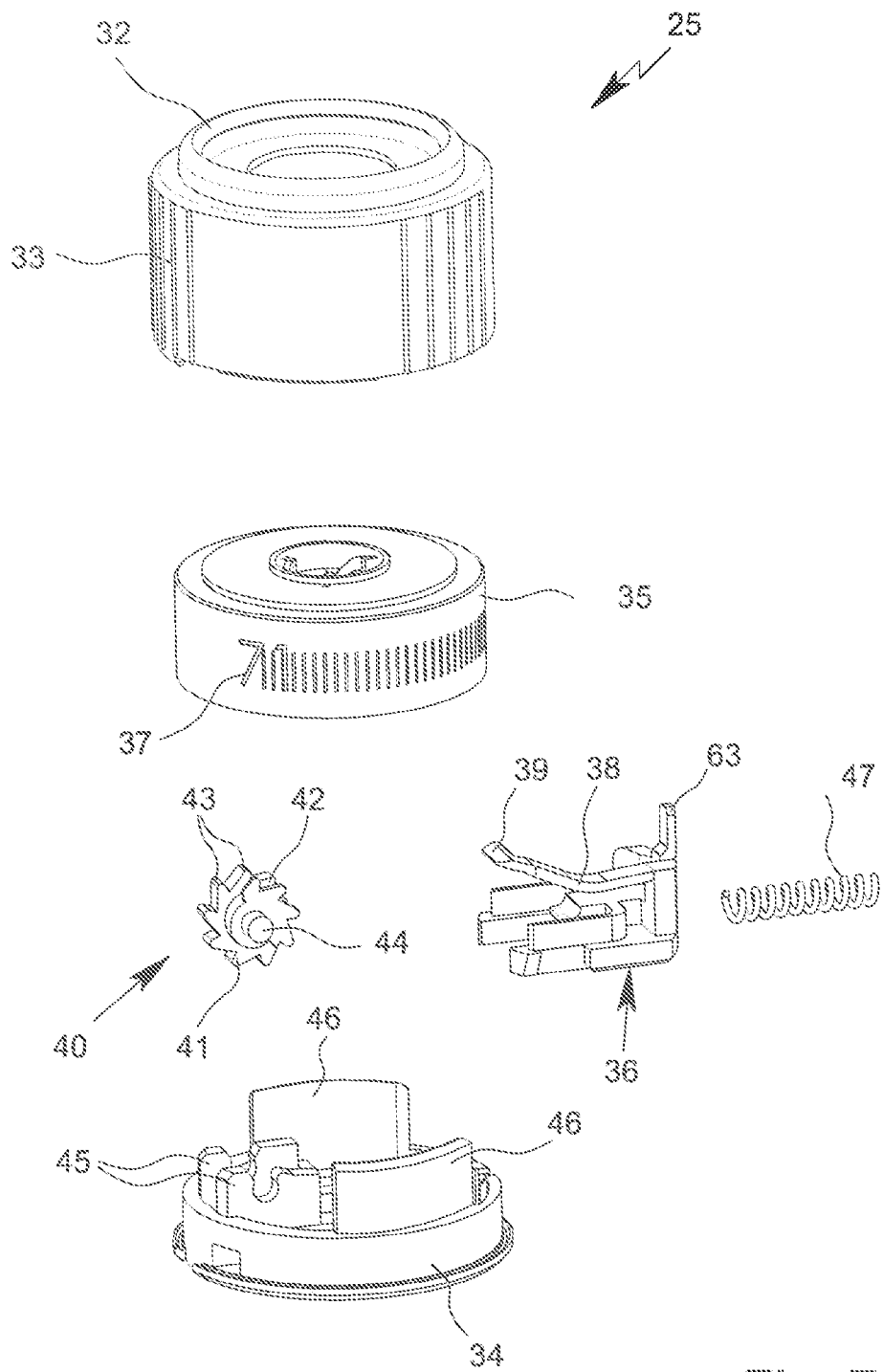
Figure 12:
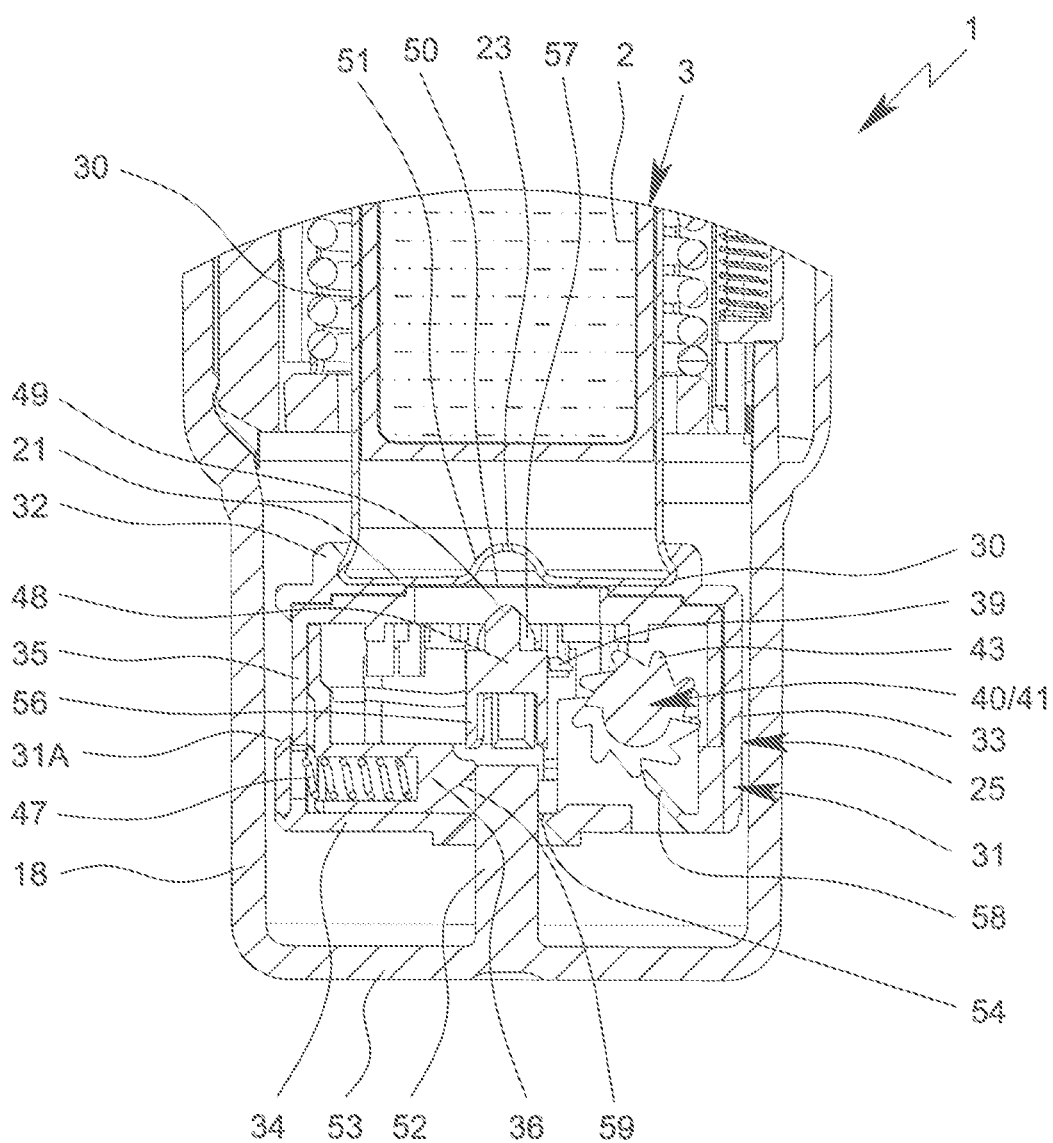

FIG. 12 shows in a partial enlargement similar to FIG. 4 a lower portion of the nebulizer 1 in an intermediate state after partial tensioning. The indicator device 25 is in an actuated state as shown in FIG. 8 (second position).

The nebulizer 1 or housing part 18 comprises preferably a driving part 52 for driving or actuating the indicator device 25 when using the nebulizer 1, in particular for actuating the indicator device 25 in response to any tensioning of the nebulizer 1 and/or any (axial or stroke-like) movement of the container 3.

Preferably, the driving part 52 is arranged or formed in the housing part 18, in particular on the axial end face or bottom 53 of the housing part 18.

Preferably, the driving part 52 is arranged centrally and/or extends axially.

Preferably, the driving part 52 is at least substantially cylindrical and/or pin-like or bolt-like.

Preferably, the driving part 52 is held by the housing part 18 and/or integrally formed by the housing part 18.

In the preferred embodiment, the movement of the container 3 and, thus, of the indicator device 25 during the tensioning (downward movement in the drawings) and/or during pressurization and dispensing (upward movement in the drawings) and/or one or both of the respective end positions in the non-tensioned state and tensioned state, respectively, can be used for actuating the indicator device 25, i.e. for counting.

Preferably, the relative movement of the container 3 and/or indicator device 25 within the nebulizer 1, and more preferred the movement during dispensing, is used for actuating or triggering the indicator device 25 and/or counting.

When tensioning the nebulizer 1 and/or moving the indicator device 25 downwards, the driving part 25 enters or engages through an insertion opening 54 of the indicator device 25 or its housing 31, in particular axially.

Preferably, the driving part 52 and the insertion opening 54 are arranged centrally and/or axially aligned.

In the present embodiment, the driving part 52 actuates the actuation element 36, i.e. moves the actuation element 36 from an initial first position shown in FIGS. 3 to 6, to an actuated second position shown in FIG. 9.

Preferably, the actuation spring 47 biases the actuation element 36 into the first portion.

In the present embodiment, the actuation element 36 is moveable back and forth between the first and second positions for indexing the indicator element 35, in particular for incrementally rotating the gear 41 in one direction to respectively drive the indicator element 35. As any rotation of gear 41 is transformed in a reduced rotation of the indicator element 35, thus every movement of the actuation element 36 from the first to the second position or vice versa results in a movement of the indicator element 35.

In the present embodiment, the actuation element 36 is moveable transversally, preferably perpendicularly, to the longitudinal or dispensing direction of the container 3 or nebulizer 1 and/or to the stroke movement of the container 3 and/or indicator device 25.

Preferably, the actuation element 36 is moved from the more central first position radially outwards to the second position, in particular against the force of the associated, preferably helical actuation spring 47 biasing the actuation element 36 in opposite direction.

In the second position, the actuation element 36 has been moved with its actuation arm 38 or actuation portion 39 out of engagement with gear 41 as indicated in FIGS. 8 and 12.

Figure 13:
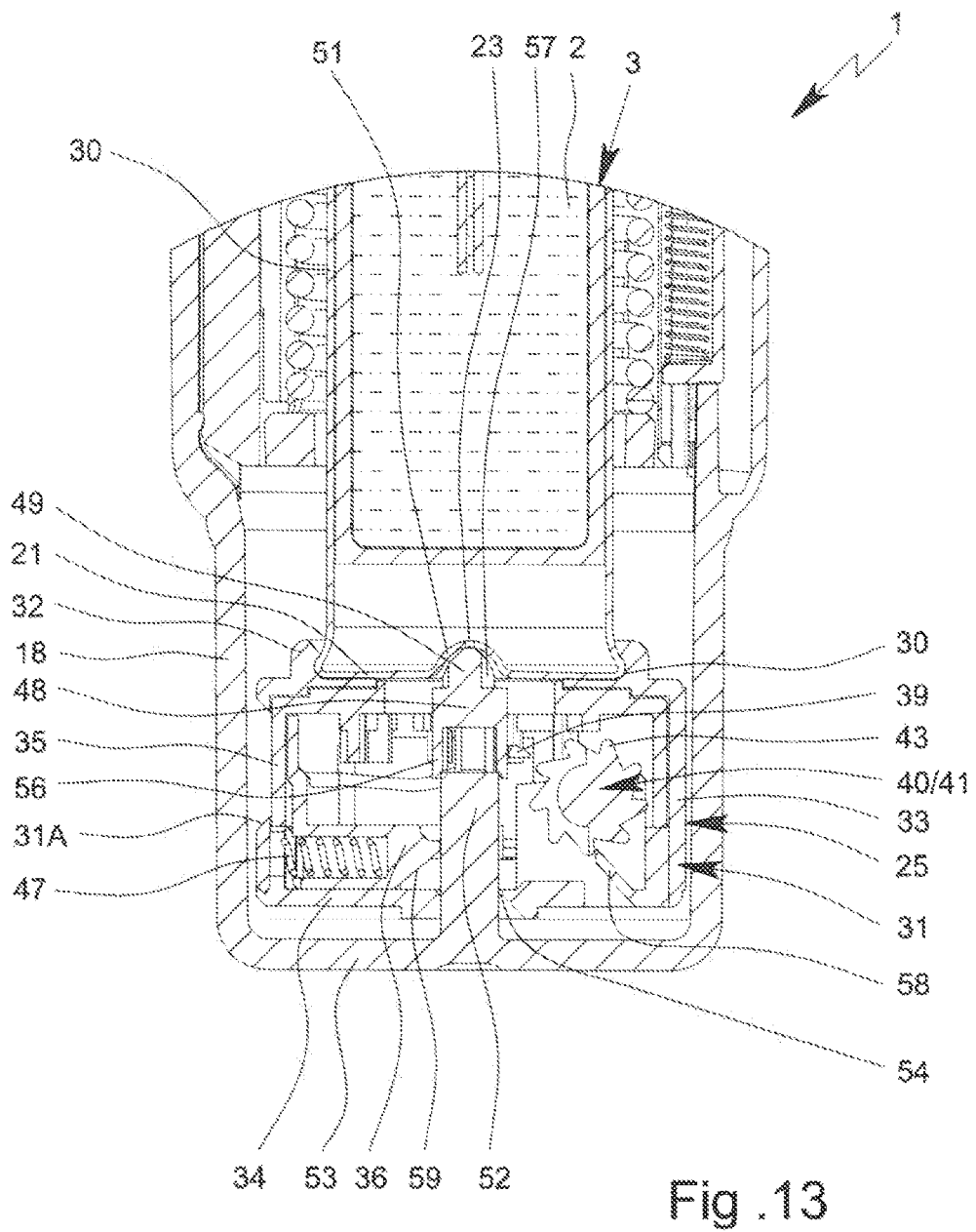

FIG. 13 shows in a similar enlarged section as FIG. 12 the fully tensioned state.

In the (fully) tensioned state, the container 3, more precisely the aeration opening or venting hole 23, is opened at least when the nebulizer 1 is tensioned with a container 3 for the first time.

Preferably, the opening of the container 3 or venting hole 23 for aeration is realized by piercing or breaking, in particular of foil 50.

Figure 1:
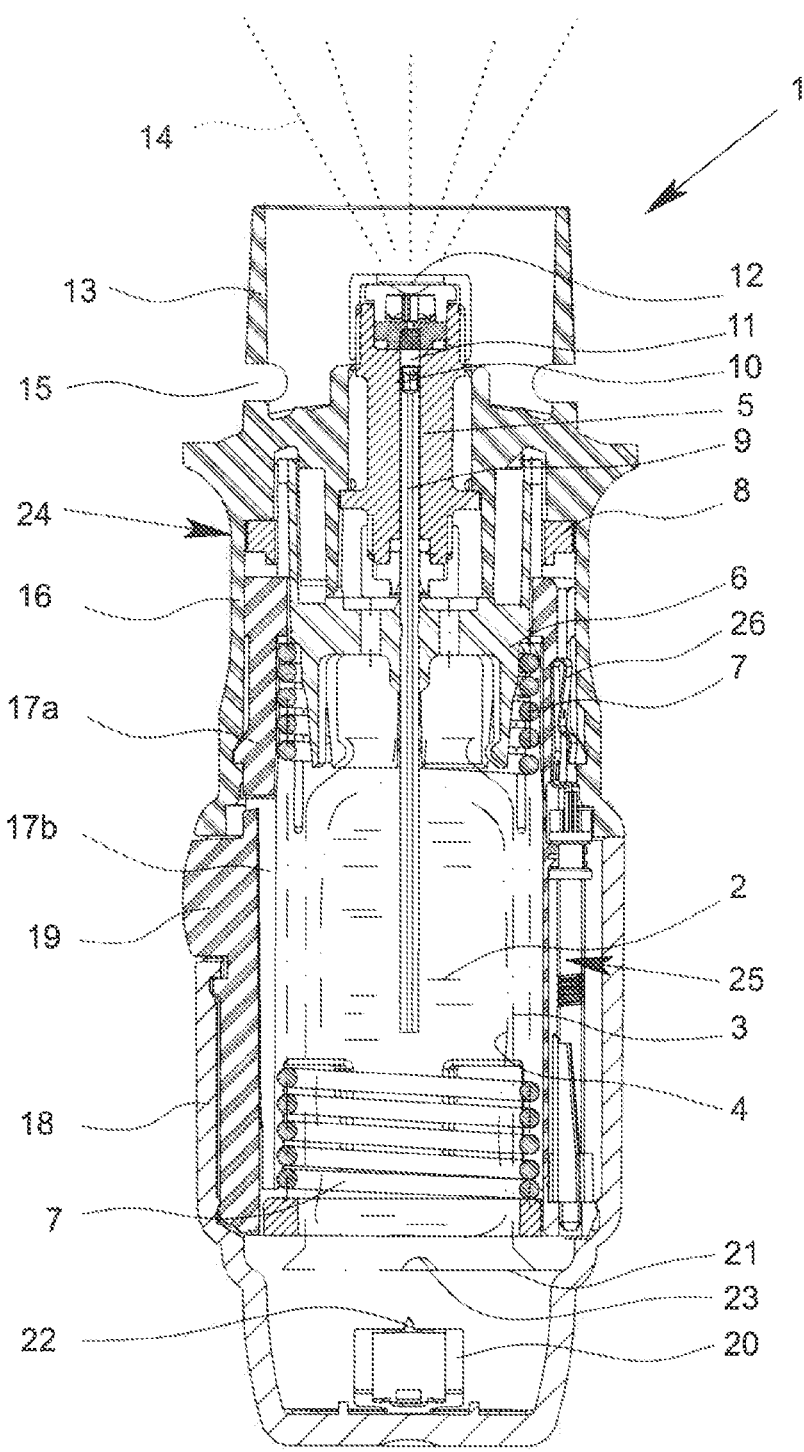
Figure 2:
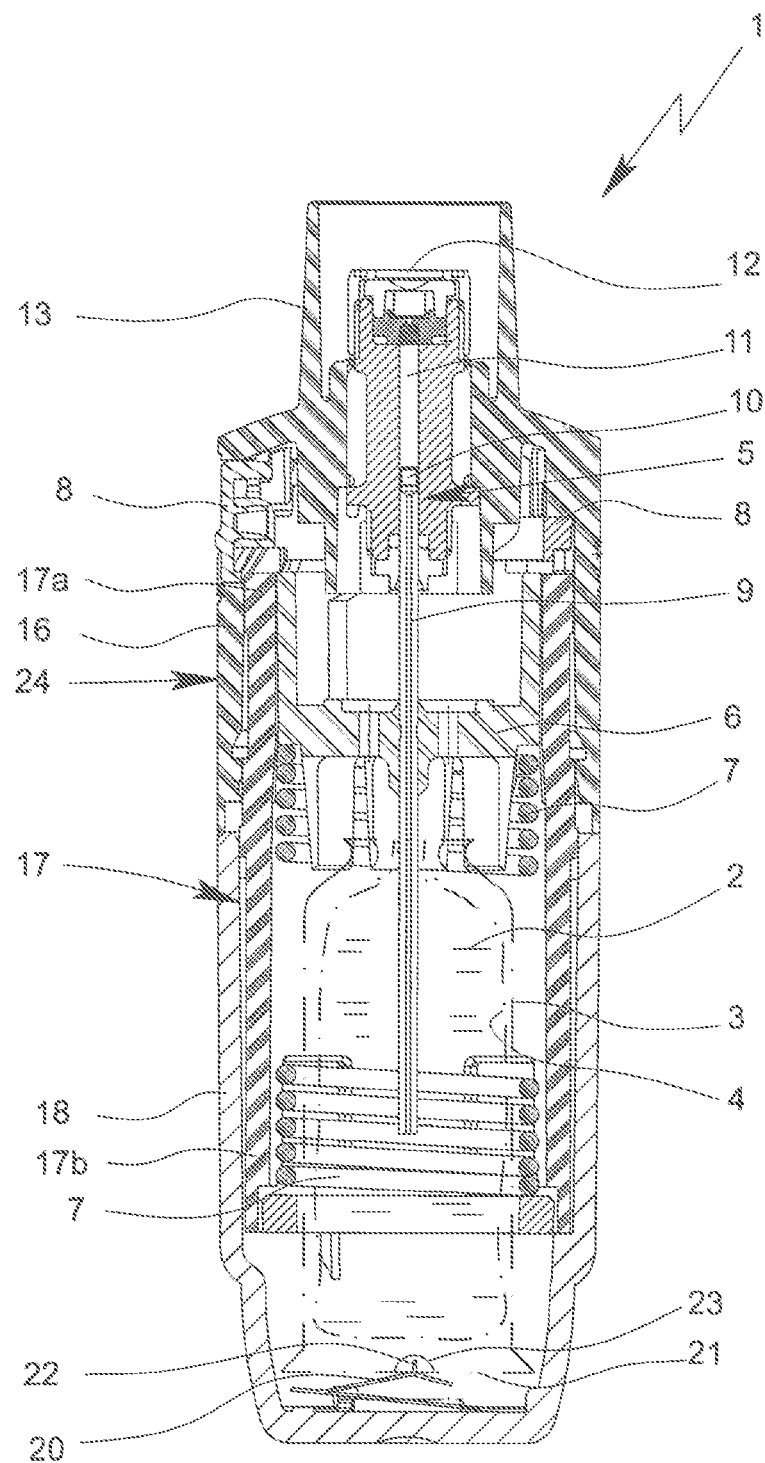
Figure 3:
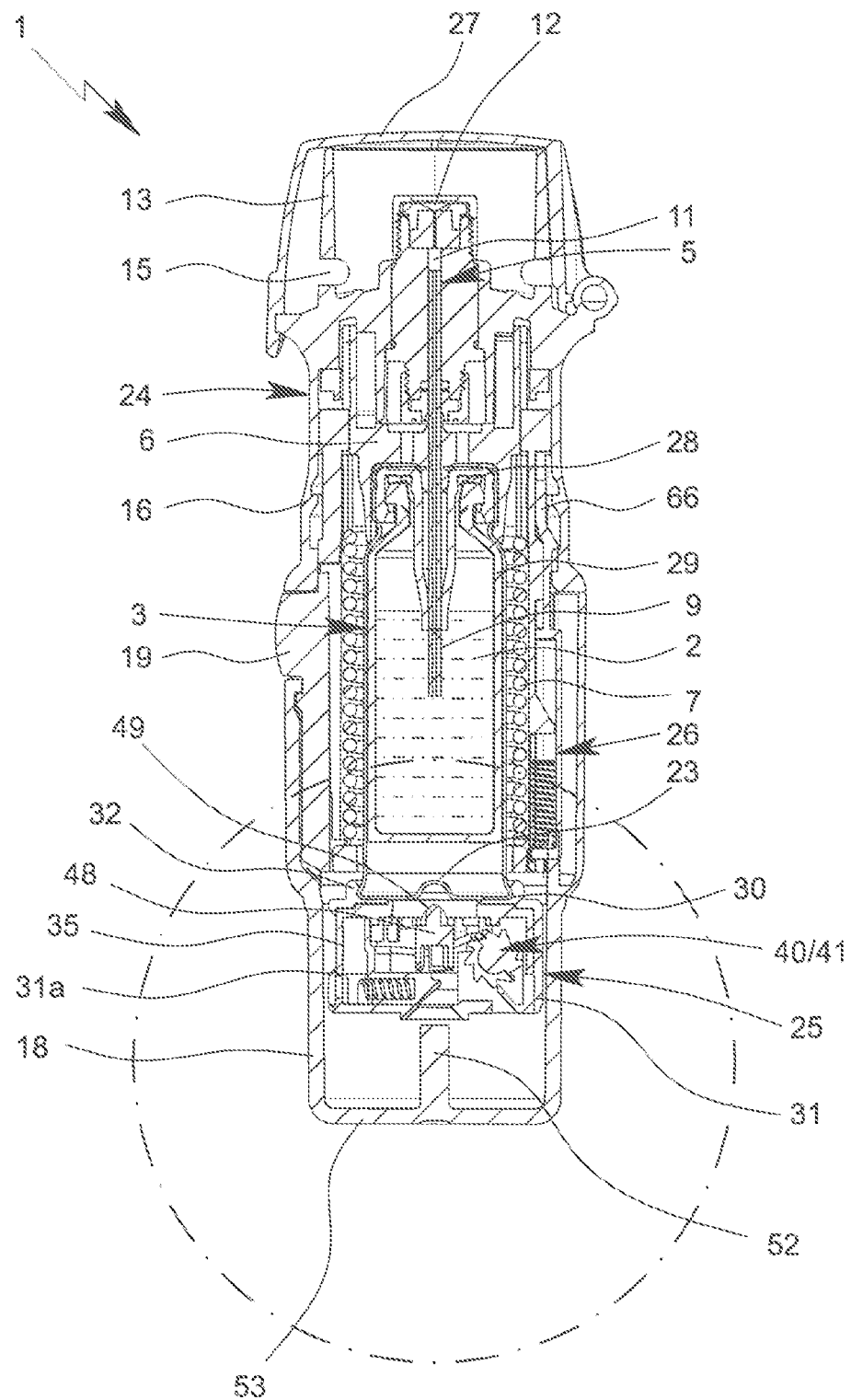

The opening or piercing can be affected directly by the driving part 52, independently therefrom, e.g. by means of the aeration spring 20 with the piercing element 22 similar to the embodiment shown in FIG. 2. Alternatively, the opening or piercing can be achieved indirectly, preferably via the piercing part 48 which is preferably actuated by the driving part 52.

Preferably, the piercing part 48 is formed as separate part and/or provided by the indicator device 25 and/or arranged within the indicator device 25.

In the preferred embodiment, the piercing part 48 is held axially moveable by a support structure 55 of the indicator device 25, housing 31, upper part 32 and/or indicator element 35, as schematically indicated in FIGS. 10 and 11.

Preferably, the piercing part 48 and/or the support structure 55 are a one-piece-construction with a further part of the indicator devices 25, e.g. with the indicator element 35 or with the indicator housing 31, especially with the upper part 33 of the indicator housing 31.

Preferably, the piercing part 48, support structure 55 and the further part of the indicator device 25 are made of plastic in an injection molding process.

Preferably, the support structure 55 comprises flexible arms or ribs for holding the piercing part 48 axially moveable.

Alternatively the piercing part 48 can be constructed as separate, axially moveable part, which is optionally spring biased in the longitudinal or axial direction away from the container 3, so that the piercing tip is retracted from the container 3 in the non-tensioned state.

The opening or piercing can be repeated each time the nebulizer 1 is tensioned, i.e. each time when the container 3 reaches its end position in the tensioned state.

The piercing part 48 may be biased into its retracted or initial position shown in FIGS. 3 to 6, in particular by a preferably integrally formed biasing arm, spring or the like, preferably by the support structure 55.

The piercing part 48 may comprise a compensation portion, such as a flexible arm 56, for compensating any tolerances in axial direction. The compensation portion allows axial compression—here by radial flexing of arms 56—when a predetermined axial force is exceeded in order to avoid any damage of the container 3 and/or any other component of the nebulizer 1. Thus, in the preferred embodiment the driving part 52 first moves the piercing part 48 towards the container base 21 into the piercing position and further axial movement of the driving part 52 is compensated by the compensation portion, preferably by the flexible arms 56 being spread radially outwards, giving way to the tip of the driving part 52 for entering a central recess in the piercing part 48 (on the side opposite to the piercing tip 49).

The piercing part 48 comprises preferably at least one axial channel, in particular one or more axially extending grooves 57 circumferentially distributed around the circumference of tip 49, in order to ensure unblocked aeration or venting even if the piercing part 48 stucks or stays in the foil 50 or piercing position.

Figure 14:
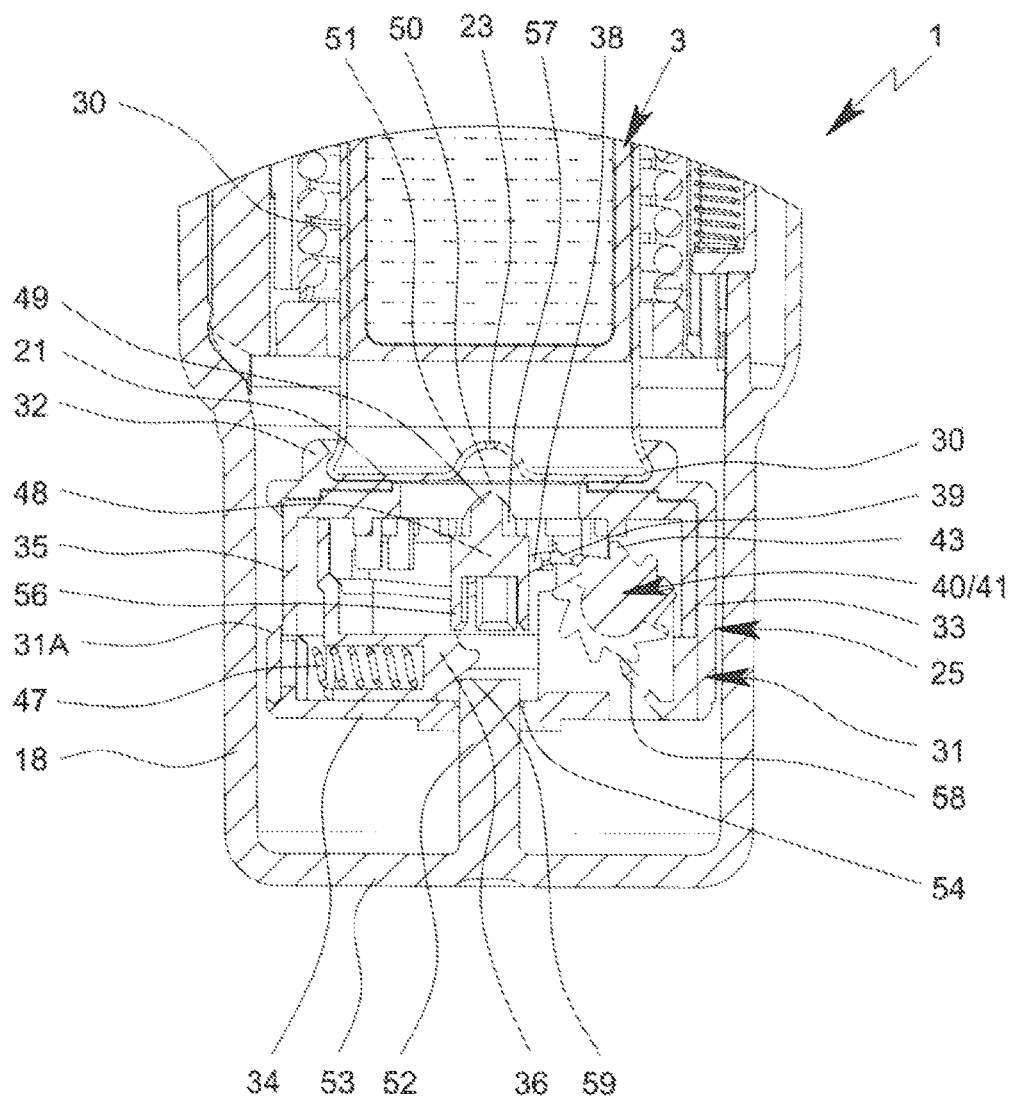

FIG. 14 shows in a similar enlargement as FIGS. 4, 12 and 13 an intermediate state of the pressurization or dispensing process, i.e. when the container 3 has been moved partially upwards again. In this state, the driving part 52 has been withdrawn from the indicator device 25 or through the insertion opening 54 partially such that the actuation element 36 starts to return to its initial or first position due to the force of the actuation spring 47. Finally, after sufficient withdrawal of the driving part 52, the actuation element 36 returns into the first position shown in FIGS. 3 to 6 when the back movement is completed.

The back movement of the container 3 and/or of the actuation element 36 actuates preferably the indicator device 25 or gear 41 and/or is detected or counted. In particular, the actuation element 36 or its arm 38 or actuation portion 39 transmits the back movement or movement from the second to the first position to the transmission 40. In particular, this movement causes an incremental rotation of gear 41.

In the present embodiment, the actuation arm 38 or its portion 39 abuts against one tooth 43 of gear 41 during the back movement and, thus, turns the gear 41 due to the back movement one step further, in the drawings in clockwise direction.

Preferably, the indicator device 25 comprises a ratchet 58 providing any counter-rotation of the transmission 40 or gear 41. Into the present embodiment, the ratchet 58 is formed by a flexible arm extending from the housing 31, in particular lower housing part 34, and/or meshing with or engaging into the gear 41 or its teeth 43.

In the end position, i.e. in the non-tensioned state, the driving part 52 is preferably further or completely retracted from the indicator device 25, the indicator housing 31 and/or insertion opening 54 as shown in FIGS. 3 to 6.

The transmission 40 or gear 41 transforms the actuation, in particular the (backward) movement of the actuation element 36 or its arm 38/actuating portion 39, into an indexing of the indicator element 35. The transmission ratio or transmission function of the transmission 40 or gear 41 may be designed or constructed such that a reduction or non-linear driving or indexing is achieved. In the present embodiment, the transmission 40 or gear 41 forms preferably a worm drive for achieving a desired reduction.

The movement of the actuation element 36—in particular from the first position to the second position—results in that the actuation arm 38 or its actuation portion 39 are moved out of engagement with the gear 41, in particular can be pulled over the next tooth 43. Hereby, the arm 38 is flexed out. The subsequent movement in opposite direction, i.e. the back movement or movement from the second to the first position, results in that the actuation arm 38 or its actuation portion 39 contacts the next tooth 41 and can transmit the at least essential linear movement of the arm 38, more precisely the preferably linear movement of the actuation element 36, into a rotation of the gear 41, more precisely in an indexing of gear 41 by preferably one tooth 43.

Preferably, the teeth 43 are asymmetrical, i.e. comprise differently inclined shoulders on one side and the other side in order to facilitate and/or ensure the incremental actuation and movement in one rotational direction by the back and forth movement and engagement of the actuation arm 38.

Preferably, the actuation element 36 is linearly moveable and/or forms a sliding carriage.

Preferably, the actuation element 36 is supported and/or held moveably by the housing 31, in particular lower part 34 of the housing 31. However, other constructional solutions are possible as well.

The actuation spring 47 acts preferably between the housing 31 or lower part 34 on one hand and the actuation element 36 on the other hand.

In the present embodiment, the spring 47 is preferably already compressed and/or biased in the first position and/or biases the actuation element 36 such that it at least partially closes or blocks the insertion opening 54.

Preferably, the actuation element 36 comprises an inclined gliding surface 59 at its part protecting into or over the insertion opening 32 in the first position. This surface 59 is inclined such that the insertion of the driving part 52, i.e. its axial movement or abutment, is transformed into a transversal or radial movement of the actuation element 36.

Alternatively or additionally, such a surface 59 can also be formed at the driving part 52 to achieve the desired transformation of the axial movement into a transversal or radial movement by means of an inclined plane.

Therefore, the actuation or rotation of the transmission 40 or gear 41 is preferably effected by the force of the actuation spring 47 or any other pressure or energy store or spring means. This results in the advantage that no additional force is necessary for driving the indicator device 25 or its indicator element 35. Consequently, the pressurization and dispensing process is not disturbed.

Further, the triggering of the counting or actuation of the transmission 40/gear 41 is effected preferably by the pressurization or dispensing process or movement, i.e. during the actual dispensing of fluid 2, i.e. usually during actual use or inhalation.

The actuation spring 47 biases the actuation element 36 preferably towards closing the insertion opening 54.

Usually, the movement of the actuation element 36 is restricted so that it does not completely close the insertion opening 54 before the locked state is reached. This limitation is realized in the present embodiment preferably via a control means or portion 62 against which a control part 63 abuts in particular to restrict the back movement of the actuation element 36 at the first position.

The abutment is shown in particular in FIG. 10. However, other constructional solutions are possible as well.

After the number of uses of the nebulizer 1 with the container 3 has reached or exceeded a predetermined number of uses as detected or registered by the indicator device 25, a locked state is entered and the nebulizer 1 will be locked against further use with the current container 3 and/or the container 3 will be locked against further use with the nebulizer 1.

Figure 15:
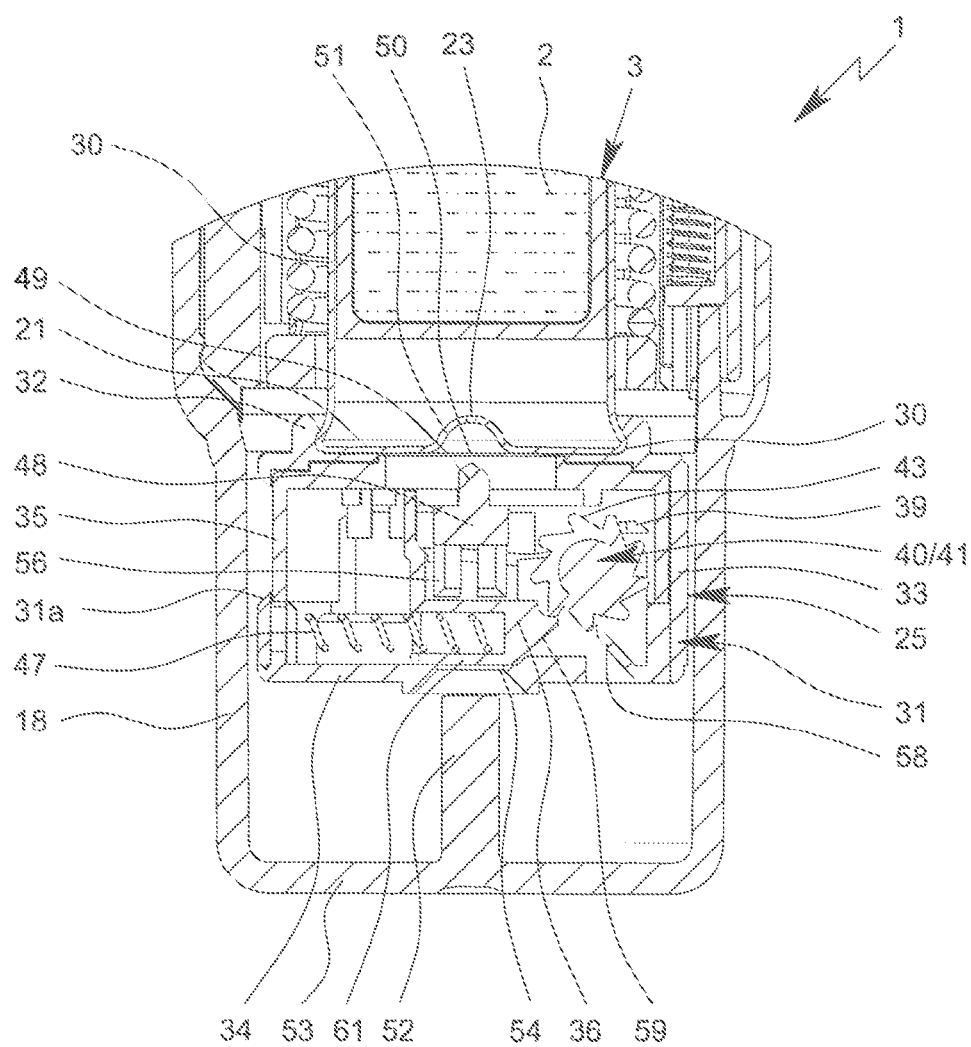

In particular, the indicator device 25 comprises a blocking part 61 which blocks further use of the container 3 and/or closes or blocks the insertion opening 54 in the locked state as schematically shown in the schematically enlargement of FIG. 15 which shows a similar part as FIGS. 4 and 12 to 14. In this shown state, the container 3 has returned to its non-tensioned position and the driving part 52 has been retracted from the indicator device 25. During the last dispensing or pressurization process, the indicator device 25 has moved the indicator element 35 one step further and detected or registered that the predetermined number of uses has been reached or exceeded and, thus, that the locked state shall be entered.

In the present embodiment, the indicator element 35 comprises preferably a control portion recess 62 which releases the actuating element 36 for detection of the locked state which results in locking the nebulizer 1 or current container 3 against further use.

Preferably, the control portion 62 comprises a cut out which allows or initiates movement of the blocking part 61 into a blocking position. Preferably, the blocking part 61 blocks or closes the insertion opening 54 in the blocking position, i.e. in the locked state. Preferably the control portion 62 is a wall or ridge on the inside of the rotatable indicator element 35.

Preferably, the blocking part 61 is integrated into the indicator device 25 or its housing 31.

The blocking part 61 is preferably moveable transversally or perpendicular to the longitudinal or dispensing direction of the container or nebulizer 1 and/or of the direction of stroke movement of the container 3.

Preferably, the blocking part 61 blocks the actuation or insertion movement of the driving part 52, in particular relative to the indicator device 25 and/or (sufficient) insertion of the driving part 52.

Preferably, the blocking part 61 is linearly moveable and/or formed by a sliding carriage. However, other constructional solutions are possible as well.

Preferably, the blocking part 61 is biased into its blocking position, in the present embodiment preferably by actuation spring 47 or any other suitable biasing means.

Preferably, the blocking part 61 closes or blocks the insertion opening 54 of the indicator device 25 after the last dose of fluid 2 has been dispensed and when the locked state has been entered or detected. This detection is preferably realized in that the blocking part 61 or any associated component, such as control part 63, can pass the control portion 62 in the locked state, most preferably by spring force, in particular by the force of actuation spring 47 or the like, as schematically shown in FIG. 11.

Preferably, the blocking part 61 is connected with or formed by the actuation element 36 or vice versa. Most preferably, the blocking part 61 forms a wall or side, preferably flat side, of the actuation element 36. However, other constructional solutions are possible as well.

In the present embodiment, the actuation element 36 can move in the locked state from the first position into the third position, i.e. preferably in the opposite direction than the movement into the second position.

In the present embodiment, the actuation element 36 can close the insertion opening 54 preferably completely in the third position (blocking position).

With other words, the blocking position of the blocking part 61 corresponds preferably to the third position of the actuation element 36.

In the locked state or third position, the actuation element 36 has moved with the actuation arm 38 or its portion 39 further in the actuation direction so that the actuation portion 39 has passed the previous tooth 43 in the rotation direction of gear 41 as indicated in FIG. 15.

Preferably, the actuation element 36 is constructed to block further use of the container 3 in the locked state or third position (blocking position).

Preferably, the actuation element 36 is moveable back and forth between the first and second position for indexing the indicator element 35 and is moveable into a third position to block further use of the container 3 in the locked state.

In particular, the closed indicator device 25 or blocking part 61 results in particular in that the container 3 cannot move inside the closed housing of the nebulizer 1 in the stroke-like fashion as previously and as required for normal or further use so that normal use is prevented.

In particular, the locking of the indicator device 25 or insertion opening 54 results in that the nebulizer 1 or housing part 18 is at least partially opened when the nebulizer 1 is tensioned once more or when it is partially tensioned. FIG. 16 shows this state (partially tensioned nebulizer 1 with partially opened housing part 18) in a schematic, longitudinal section of the nebulizer 1. During the tensioning process the container 3 is moving downwardly together with the indicator device 25. Starting from the non-tensioned state (upper position of the container 3), the indicator device 25 abuts soon with its blocking part 61/actuating element 36 against the member usually actuating the indicator device 25, here the driving part 52, so that a further usual downward movement is not possible.

In particular, the blocking part 61 restricts the axial movability of the container 3 in the nebulizer 1 in the locked state, preferably by preventing the driving part 52 from insertion into the indicator device 25 or restricting its insertion in the locked state. Due to the force applied when tensioning the nebulizer 1 and due to the resulting axial force in the movement of the container 3, the housing part 18 will be moved outwards or relative to the nebulizer 1, inner part 17 or upper part 16 together with the container 3 and indicator device 25 during the further tensioning movement in axial direction in the locked state.

The above common downward movement of container 3, indicator device 25 and housing part 18 is possible due to a respectively constructed fastening of the housing part 18 at the nebulizer 1. In particular, the retaining force is selected or set such that it can be overcome by the downward movement of the container 3.

In the present embodiment, the retaining element 19 engages with a retaining nose 64 in a respective retaining recess 65 in the housing part 18 or vice versa. Thus, substantially an undercut can be realized. However, the abutting shoulders which extend at least essentially radially of the nose 64 on one hand and the recess 65 on the other hand are slightly inclined, preferably by about 1° to 5° to the radial plane such that the axial force of the tensioning process can overcome the retaining force provided by the engagement of the nose 64 into the recess 65 so that the retaining element 19 is flexed radially and the retaining engagement is overcome. Consequently, the housing part 18 is moved downwardly as well and, thus, is pushed at least partly from the nebulizer 1 or separated from the upper housing part 16 and/or pushed from the inner part 17.

This pushing or axial displacement of the housing part 18 or any other opening of the nebulizer 1 results preferably in that the nebulizer 1 is locked against further use by means of the locking device 26. Therefore, the indicator device 25 or its blocking part 61 effect, indirectly via the opening of the nebulizer 1, the desired locking of the nebulizer 1 in the locked state.

However, a (more) direct actuation of the locking, in particular of the locking device 26 is possible as well. For example, the indicator device 25 or its actuation element 36 or blocking part 61 can directly act on or actuate the locking device 26 when entering the locked state or in the locked state.

In the preferred embodiment, the locking device 26 blocks tensioning of the nebulizer 1 in the locked state.

Preferably, the locking device 26 comprises a moveable locking element 66 and an associated locking spring 67. The locking element 66 is preferably axially moveable between a locked position and an unlocked position. The locking element 66 is preferably biased into the locked position by the locking spring 67.

Figure 16:
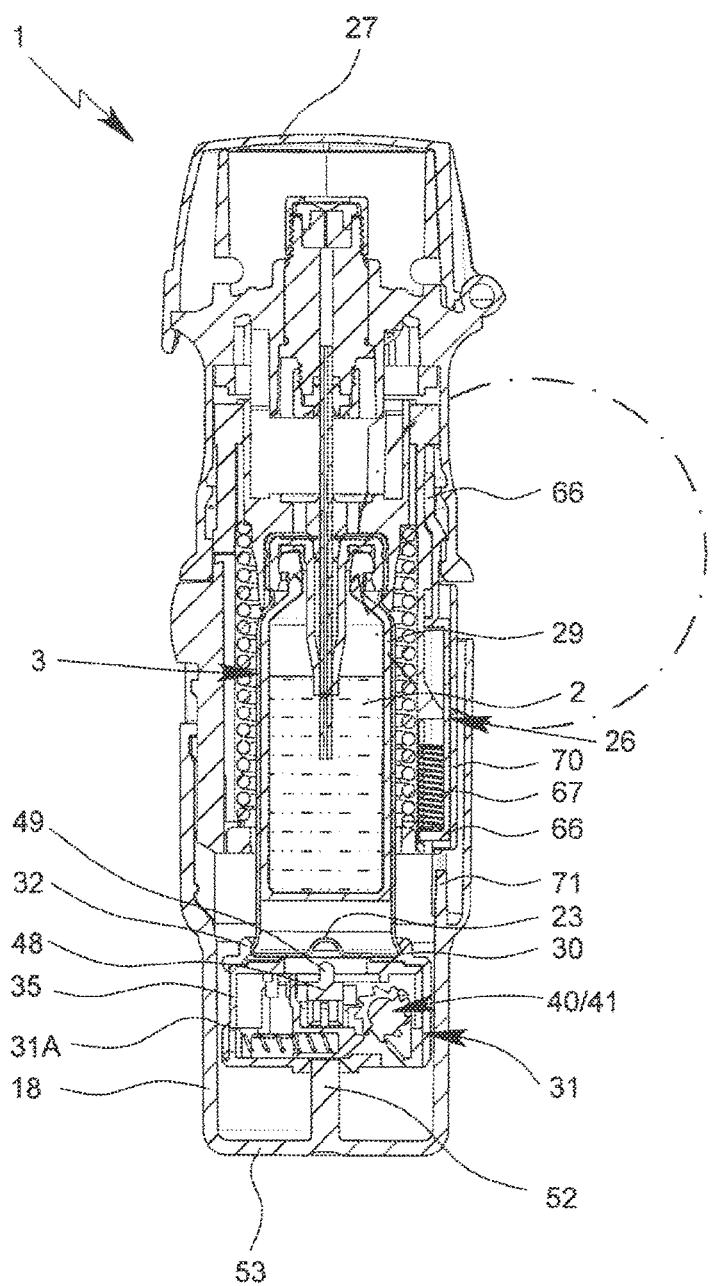
Figure 17:
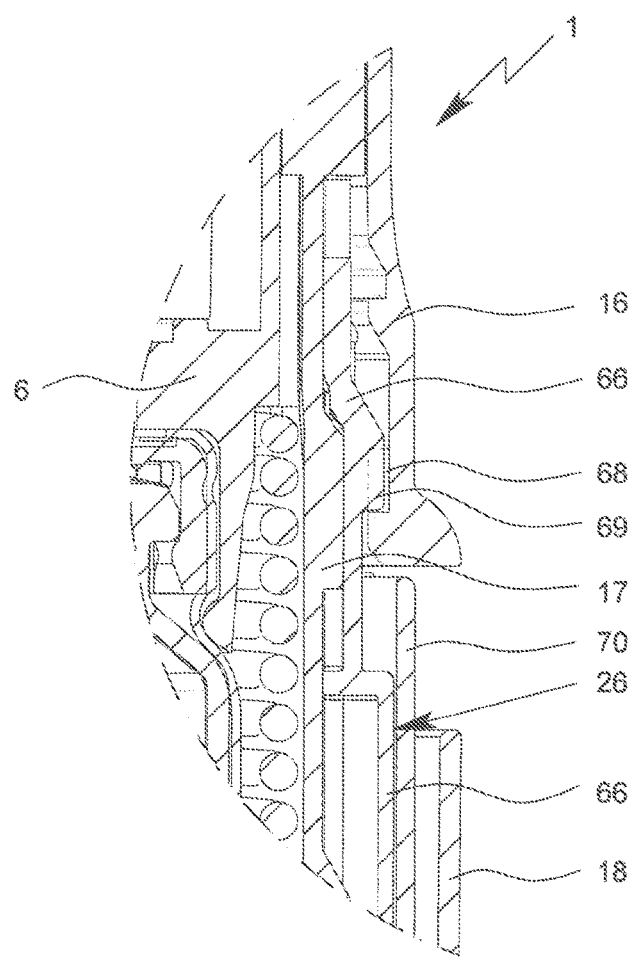

In the locked position, the locking element 66 is preferably in its lower axial position shown in FIG. 16. FIG. 17 shows an enlargement of the encircled area of FIG. 16.

In the locked position, the locking element 66 blocks rotation of the inner part 17 relative to the outer part 16 and, thus, blocks (further) tensioning of the nebulizer 1. This is preferably achieved in the present embodiment in that the locking element 66 moves or engages preferably axially into a respective pocket 68 formed in the upper part 16 such that said relative rotation is blocked. In particular, the locking element 66 engages with an engagement portion 69 into the respective recess or pocket 68 such that any further rotation and/or back rotation is prevented. However, other constructional solutions are possible as well.

Preferably, the nebulizer 1 or upper part 16 may be enforced by one or more metallic inserts or enforcement elements, which may be ring-like and/or may extend in circumferential direction and/or may be arranged adjacent to or around the pocket 68 and/or adjacent to the lower or free end of the upper part 16.

The locking device 26, in particular the locking element 66 and the locking spring 67, are preferably arranged and/or supported by the inner part 17 and/or extend between the inner part 17 and upper part 16.

The nebulizer 1, inner part 17 or locking device 26 comprises preferably a cover 70 covering the locking device 26 at least on the periphery of the lower part 17b of the inner part 17 in order to prevent or at least complicate any undesired manipulation of the locking device 26 or locking element 66 by a user or patient.

Preferably, the locking device 26 or locking element 66 is locking relative rotation or further rotation before the complete tensioned state or position is reached, i.e. preferably in an intermediate position, most preferably in the second half of the total rotation angle necessary for tensioning the nebulizer 1 by turning the lower housing part 18 relative to the upper housing part 16.

This intermediate blocking has the advantage that it is preferably not possible to fully actuate the nebulizer 1 as it is not possible to reach complete tensioning and, thus, the gear or transmission transforming the relative rotation into the axial stroke of the holder 6 actually holds the holder 6 in the intermediate position and does not allow any axial back movement into the upper, non-tensioned position.

However, it is also possible that the locking device 26 locks the nebulizer 1 against further tensioning after the complete tensioned state has been reached.

Alternatively or additionally, it is also possible that the locking device 26 or its locking element 66 locks the release of the spring 7 or holder 6 to dispense the fluid 2, in particular by locking any depression of blocking element 8 and, thus, blocking the release. However, other constructional solutions are possible as well.

Figure 18:
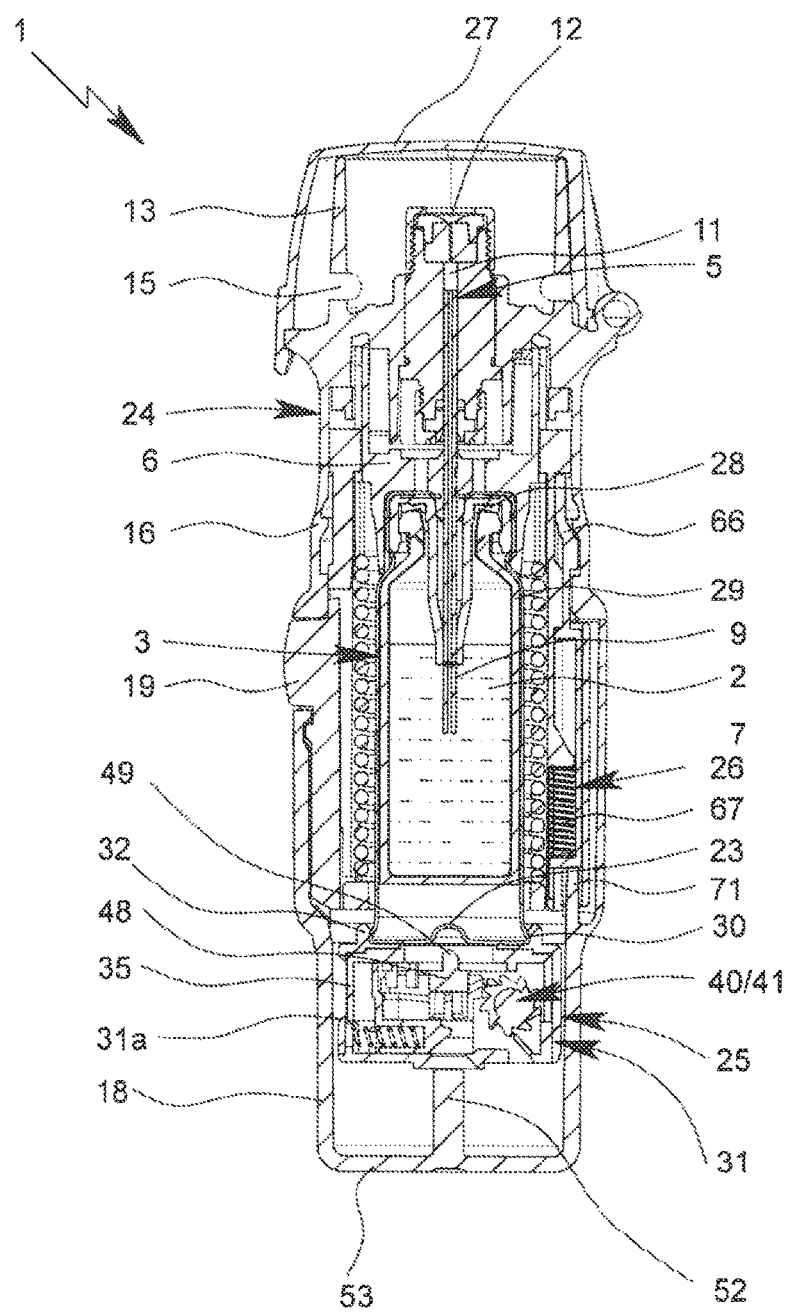

FIG. 18 shows the nebulizer 1 in a similar schematic section as FIG. 16, however with the locking device 26 in the unlocked position, i.e. the locking element 66 in the upper position. The locking device 26 or locking element 66 is brought into this position or unlocked preferably only by closing the nebulizer 1, in particular by the housing part 18 in the completely attached or closed position.

In the shown embodiment, the housing part 18 comprises a preferably finger-like and/or axially extending actuator 71 which extends into the locking device 66 and/or into the cover 70 and/or axially abuts and/or pushes the locking element 66 into its unlocking position (upper position), as shown in FIG. 18. Thus, only the completely closed nebulizer 1 or housing part 18 unlocks the locking device 26 and, thus, unlocks the nebulizer 1.

The actuator 71 is preferably arranged within the housing part 18 so that any manipulation is not possible or at least complicated.

When the nebulizer 1 is in the locked state and, preferably when the nebulizer 1 or its housing part 18 has been opened partially by the last tensioning process, any further use of the nebulizer 1 with the container 3 is not possible. The locking device 26 locks preferably automatically. Preferably, the locking spring 62 biases the locking element 66 into the locking position, so that upon at least partial opening or (axial) displacement of the nebulizer 1 or its housing part 18, the locking device 26 or its locking element 66 can move and moves into the locking position.

Preferably, the locking element 66 is moveable (essentially or only) in axial direction.

After replacement of the current container 3 with its locked indicator device 25 (blocking part 61 in the blocking position) against a new container 3 including a new or reset indicator device 25, the nebulizer 1 or its housing part 18 can be closed completely again. Thus, the nebulizer 1 or its locking device 26 can be or is unlocked again. Preferably, the actuator 71 pushes the locking element 66 back into its unlocking position.

Thus, the locking device 26 is reset or unlocked again, preferably by (completely) closing the nebulizer 1, its housing 24 or housing part 18, and the nebulizer 1 can be used with the new container 3 as previously.

In the shown embodiment, the locking element 66 is preferably formed by one single part. However, the locking device 26 may comprise multiple parts forming or containing the locking element 66.

Preferably, the container 3 is or has to be replaced in an at least partially tensioned state of the nebulizer 1, in particular such a tensioned state that complete closing of he nebulizer 1 or its housing 24 is not possible when the indicator device 25 is in the locked state or when the insertion opening 54 is closed.

In the present embodiment, the locking element 66 is axially moveable between the locking and non-locking position and vice versa. However, the locking element 66 can be moveable alternatively or additionally in radial direction to switch between the locking and non-locking position or vice versa. For example, the locking element 66 may be pushed radially outwards, in particular to engage in a respective groove or recess or the like in the locking position, in order to block (further) tensioning or use of the nebulizer 1.

In particular, the locking element 66 may form or may be formed by a sliding block.

In the present embodiment, the locking spring 67 is preferably arranged at the lower part 17b of the inner part 17 and/or at the lower end of the locking device 26 or locking element 66, or near or adjacent to the housing part 18. However, the locking spring 67 can also be arranged at the other end and/or within the upper housing part 16 of the nebulizer 1 and/or at any other convenient location.

In the present embodiment, the locking spring 67 is preferably a push-spring. However, a pull-spring could be used alternatively.

In the present embodiment, the locking spring 66 is preferably a helical spring. However, it could be used alternatively e.g. a flat spring or leaf spring or any other spring.

In the present embodiment, the locking element 66 and the locking spring 67 are forming by separate parts. However, it is generally also possible to integrate the locking element 66 into the locking spring 67 or vice versa.

It has to be noted that the indicator device 25 or its actuation element 36 or blocking part 61 can actuate also directly the locking device 26, in particular via a mechanical connection or coupling (not shown), in the locked state or when entering the locked state, or vice versa.

It has to be noted that the piercing part 48 is preferably received within the indicator device 25 or its housing 31, but can protrude outwards in the actuated state.

It has to be noted that the insertion opening 54, which is preferably arranged centrally and/or opens in axial direction and/or allows axial insertion of an actuator element, in particular the driving part 52 in the present embodiment, can also be formed as a recess, groove, indention or the like and/or can be arranged at any position or location at the indicator device 25 with any orientation.

Alternatively, the insertion opening 54 or its closing can also be omitted. Instead, the indicator device 25, actuation element 36 or blocking part 61 can more or less directly communicate with or actuate the locking device 26 or, for example, the retaining element 19 or blocking element 8 in order to cause a direct or indirect locking of the nebulizer 1 or container 3 against further use.

Figure 19:
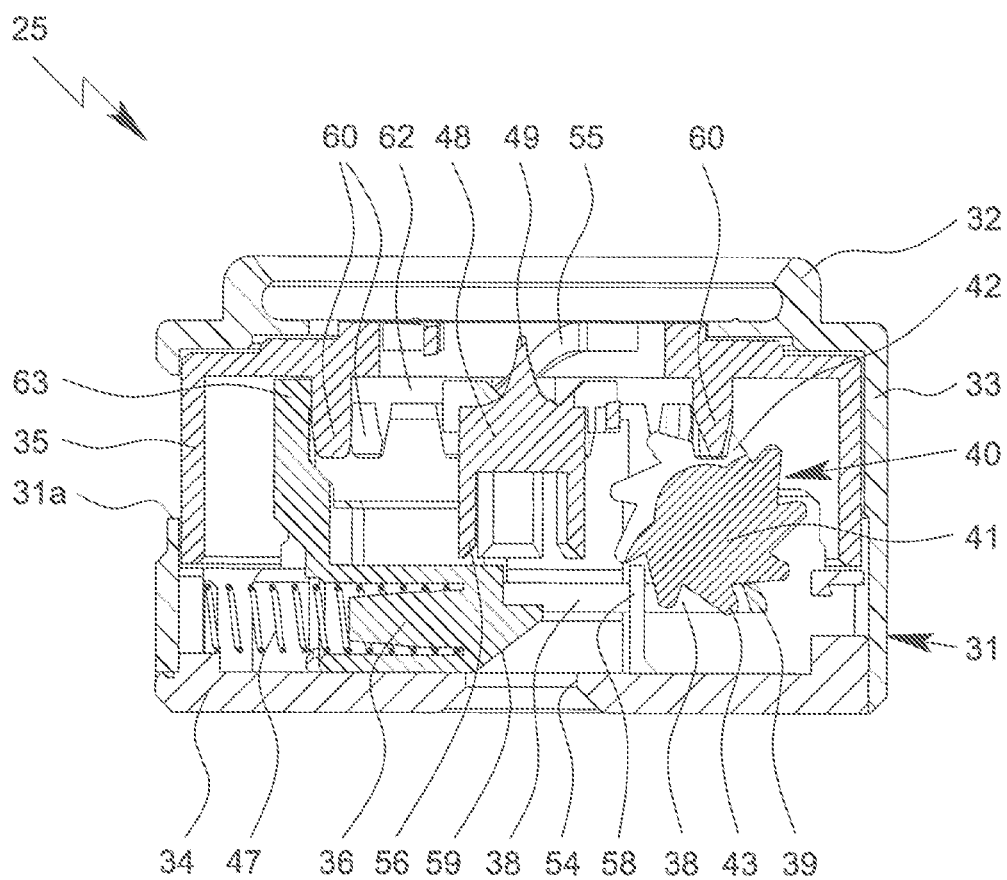
Figure 20:
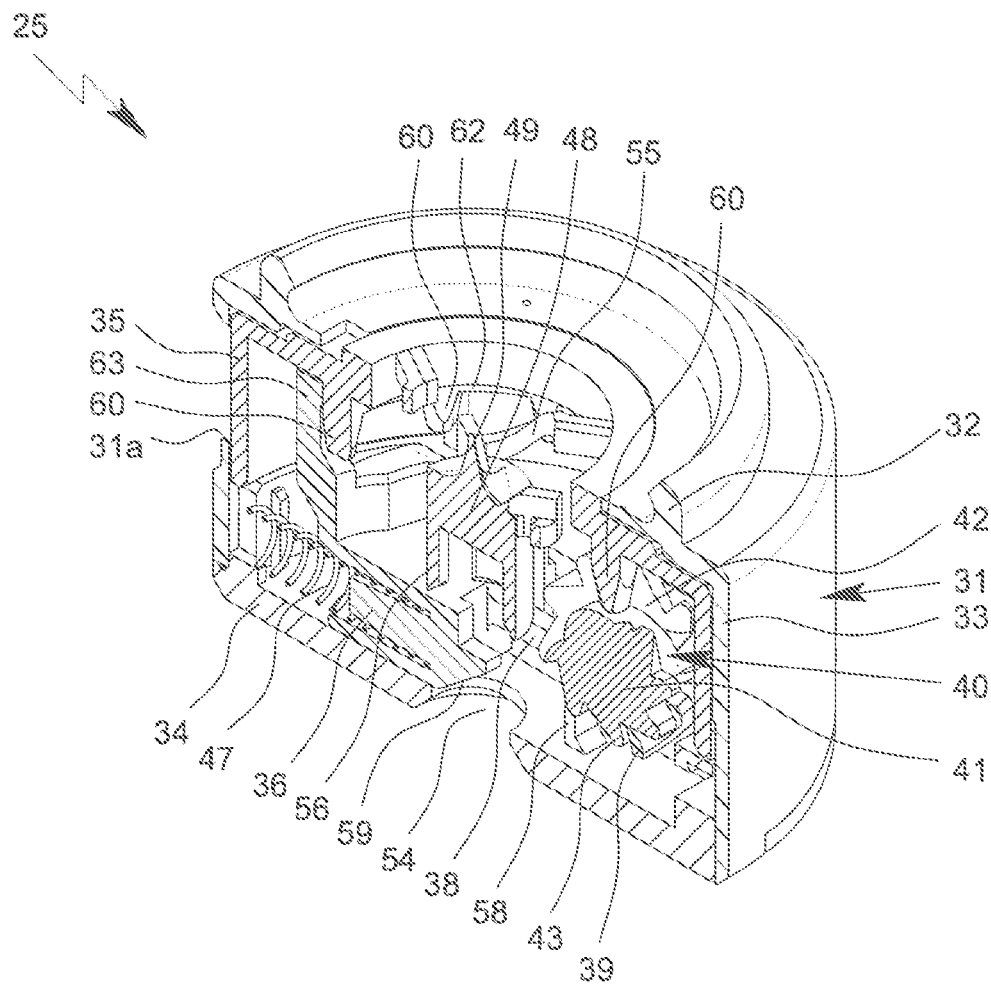

FIG. 19 shows in a schematic section the indicator device 25 according to a modified embodiment of the present invention. FIG. 20 shows a perspective view of the section according to FIG. 19.

In the following, only relevant differences are described so that the previous explanations and aspects apply in addition, in particular in the same or similar manner, without repetition.

In the modified embodiment, the actuation arm 38 and actuation portion 39 do not engage inbetween the worm drive, i.e. between the gear 41 and the engaging protrusions 60 of the driven part, here namely the indicator element 35, but engage with or actuate the gear 41 on another side or the side opposite the worm drive, here preferably in FIG. 19 from below and not from above. In particular, the actuation arm 38 extends more or less in a radial plane and/or more or less in a common plane with the actuation spring 47 and/or blocking part 61 or the sliding carriage part of the actuation element 36.

Preferably, the actuation arm 38 or portion 39 engages with the gear 41 on the side opposite the container 3 or gripping section 32.

In the modified embodiment, the indicator device 25 counts preferably when the nebulizer 1 is tensioned, i.e. during the tensioning process and not during the dispensing process as provided in the initial embodiment of the present invention.

In particular, the actuation element 36 or its arm 38 drives or rotates the transmission 40 or gear 41, when the driving part 52 is inserted into the indicator device 25, its housing 31 or its insertion opening 54 and/or when the actuation element 36 is moved from the first position to the second position and/or when the actuation element 36 is pushed transversally by the driving part 52. In the opposite direction, the actuation arm or its actuation portion 39 passes the next tooth 43 of the gear 41, i.e. does not drive the gear 41.

In the modified embodiment, the indicator device 25 or counting is not driven by the force of the actuation spring 47 or any other spring or energy store, but by the relative movement of the indicator device 25 within the nebulizer 1 or by the insertion of an actuator element, such as the driving part 52. However, other constructional solutions are possible as well.

In the modified embodiment, the blocking of the carriage/actuation element 36/locking part 61 to move into the third or locking position are released during the tensioning when a predetermined number of uses is reached or exceeded. Then, the carriage/actuation element 36/blocking part 61 abut against the driving part 52 because the counting occurs during the tensioning. When the nebulizer 1 is actuated or when the blocking element 8 is depressed, the nebulizer 1 is triggered and the (last) dose of fluid 2 is nebulized. During this nebulization, the driving part 52 is removed from the indicator device 25 or insertion opening 54 so that the carriage/actuation element 36/blocking part 61 are free to move into the third or locking position due to the force of the actuation spring 47 or any other spring means.

During the next tensioning, the nebulizer 1 or its housing 24 or housing part 18 will be partially opened when the driving part 52 abuts against the closed indicator device 25, in particular against the carriage/actuation element 36/blocking part 61 restricting or closing the insertion opening 54.

In the previous embodiment, the counting or actuating of the indicator device 25 takes place or occurs when dispensing fluid, i.e. when the driving part 52 is withdrawn from the insertion opening 54. There, the carriage/actuation element 36/blocking part 61 are released during the last use of the nebulizer 1 or dispensing, i.e. when moving from the second to the first position so that the carriage/actuation element 36/blocking part 61 can move further directly into the third or unlocking position. Thus, any later dispensing is not possible.

In both cases, i.e. in the previous embodiment and in the modified embodiment, the indicator device 25 blocks full axial or stroke-movability of the container 3 within the nebulizer 1 in the locked state and/or causes at least partially opening of the nebulizer housing 24 and/or housing part 18 in the locked state, in particular when the nebulizer 1 is tensioned at least partially for the last time with the current container 3.

Further, the at least partial opening of the nebulizer 1 or its housing 24 or housing part 18 results in that the nebulizer 1 is blocked, in particular cannot be tensioned any further or used any further, with the current container 3.

FIGS. 19 and 20 show the indicator device 26 according to the present invention in the non-actuated or initial state and/or with the actuation element 36 in the first position. The control part 63, which extends preferably upwards and/or in axial direction, abuts against the preferably ring-like control portion 62 which is preferably formed by or at the indicator element 35. Preferably, the control portion 62 has a radial distance to the outer wall of the indicator element 35 so that the control part 63 can move in between and that the actuation element 36 is free to move between the first and second positions, while the abutment of the control part 63 against the control portion 62 prevents movement of the actuation element 36 from the first position further towards the third position and/or further to (complete) closing the insertion opening 54.

Preferably, the protrusions 60 are dent-like and/or are tapered towards its free ends.

Preferably, the protrusions 60 are formed on or connected with the control portion 62.

Generally, the insertion opening 54 is provided preferably with a conical surface or edge to facilitate insertion of the driving part 52 or the like.

Preferably, the support structure 55 forms or comprises one or more flexible arms for moveably holding the piercing part 48, preferably in the center of the indicator device 25 or its housing 31 or a respective opening of the housing 31, so that the piercing part 48 is usually held inside the indicator device 25 but can move and in particular protrude outwards and/or towards the container 3 for opening or piercing aeration. However, other constructional solutions are possible.

Generally, the indicator device 25 and the container 3 form an inseparable assembly or unit, which has to be replaced completely after use, in particular after reaching the locked state. However, it is also possible that the container 3 and indicator device 25 are supplied or offered as a kit which can be assembled by the use or patient.

Generally, the indicator device 25 cannot be reset after reaching the locked state so that it cannot be reused. However, it is also possible to modify the indicator device 25 such that it can be reset and reused. In this case, the indicator device 25 has to be separated from the present container 3 and connected with a new (unused) container 3. Most preferably, such a container change would automatically reset the indicator device 25.

Generally, the actuation element 36 or blocking part 61 is moveable preferably linearly, in particular like a sliding carriage. In particular, a sliding carriage is formed.

Preferably, the sliding carriage forms a base part of the actuation element 36 or blocking part 61.

Preferably, the sliding carriage, actuation element 36 or blocking part 61 is moveably held by sliding guides 72 on opposite sides, preferably on opposite sides of the insertion opening 54, as schematically shown in FIGS. 8 and 9. Preferably, the guides 72 are formed by respective rails or the like of the housing 31 or its lower part 34 which grip over respective edges or base portions 73 of the actuation element 36 or blocking part 61 to form the desired sliding guidance. However, other constructional solutions are possible as well.

Instead of the preferably linear or sled-like moveable actuation element 36 and/or blocking part 61, any other motion, in particular a radial and/or pivotal movement, is possible, in particular for partially or completely closing the insertion opening 54.

Alternatively, the actuation element 36 and/or blocking part 61 can move outwards from the indicator device 25 or its housing 31, preferably transversally and/or at one side of the indicator housing 31 for locking at least one engagement possibility and/or actuating any other component in the locked state or for locking the nebulizer 1 and/or container 3.

Alternatively or additionally, the actuation element 36 and/or blocking part 61 can engage into or abut against a section or contour of the housing part 18 and/or nebulizer housing 24 or the like in order to restrict or prevent operation or movement in the locked state in order to block further use of the nebulizer 1 and/or container 3 in the locked state.

The actuation element 36 and/or blocking part 61, in particular also when acting radially, are preferably biased by spring 47 or any other spring means. The spring or spring means can be formed integrally and/or by plastic parts or pieces. Alternatively, a spiral or clock spring or any other spring, such as helical spring 47 or the like, could be used for biasing the actuation element 36 and/or blocking part 61, preferably into the locked state.

It is also possible that the driving part 52 directly drives or actuates the gear 41. In this case, the driving part 52 is preferably elastically supported by the housing part 18, in particular via a spring means (not shown), in particular for compensating axial tolerances and/or allowing radial or transversal flexing of the driving part 52. Additionally or alternatively, the driving part 42 may be flexible in order to allow transversal flexing for engaging with the gear 41 only in one direction of relative axial movement to the gear 41 to rotate the gear 41 only in one rotational direction.

The indicator device 25 can comprise any other counting mechanism, in particular as described in WO 2009/037085 A1, page 4, line 19 to page 10, line 13, which is incorporated herein by reference. Such a counting mechanism can also trigger, release or actuate the actuation element 36 and/or blocking part 61. When using this counting mechanism, the rotatable indicator element 35 can also release or control the release of the carriage, actuation element 36 or blocking part 61 in the locked state to move into the third or locking position or close the insertion opening 54.

It is also possible that the carriage or blocking part 61 is independent from the counting. In particular, the driving part 52 may engage the hub of the counting mechanism shown in WO 2009/037085 A1 or the like and/or drive or actuate the indicator device 25 or counting without actuating the carriage or blocking part 61. In this case, the functions are separated. The carriage and/or blocking part 61 are preferably used only for restricting or closing the insertion opening 54 in the locked state, but not for actuating or driving the indicator device 25 of its counting mechanism or transmission 40 or indicator element 35 or the like.

The container 3 or indicator device 25 or insertion opening 54 may be provided with a protection (not shown), which covers in particular the insertion opening 54 before the first use.

Preferably, the protection has to be removed before the container 3 and/or indicator device 25 can be inserted into the nebulizer 1 or housing part 18.

Preferably, the protection extends transversally over the indicator device 25 or its housing 31 and/or over the container 3 and/or has a larger diameter than the indicator device 25 and/or container 3, in particular such that it does not fit into the nebulizer 1 or housing part 18.

Preferably, the protection can be removed only irreversibly, i.e. cannot be re-connected after removal.

Preferably, the protection covers or closes the insertion opening 54 and/or the indicator device 25.

Preferably, the protection is connected to the indicator device 25 or container 3 by form-fit or force-fit and/or by a snap-fit or click-fit.

As already mentioned, individual features, aspects and/or principles of the embodiments described may also be combined with one another as desired and may be used particularly in the shown nebulizers 1 but also in similar or different nebulizers.

Features of the different embodiments can be combined or exchanged.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent, or the like.

| List of reference numerals | |
|---|---|
| 1 | nebulizer |
| 2 | fluid |
| 3 | container |
| 4 | bag |
| 5 | pressure generator |
| 6 | holder |
| 7 | drive spring |
| 8 | blocking element |
| 9 | conveying tube |
| 10 | non-return valve |
| 11 | pressure chamber |
| 12 | nozzle |
| 13 | mouthpiece |
| 14 | aerosol |
| 15 | air supply opening |
| 16 | upper housing part |
| 17 | inner part |
| 17a | upper part of inner part |
| 17b | lower part of inner part |
| 18 | housing part (lower part) |
| 19 | retaining element |
| 20 | aeration spring |
| 21 | container base |
| 22 | piercing element |
| 23 | venting hole |
| 24 | nebulizer housing |
| 25 | indicator device |
| 26 | locking device |
| 27 | mouthpiece cover |
| 28 | head |
| 29 | container housing |
| 30 | container edge |
| 31 | indicator housing |
| 31a | window |
| 32 | gripping section |
| 33 | upper part |
| 34 | lower part |
| 35 | indicator element |
| 36 | actuation element |
| 37 | marking |
| 38 | actuation arm |
| 39 | actuation portion |
| 40 | transmission |
| 41 | gear |
| 42 | worm |
| 43 | tooth |
| 44 | axle section |
| 45 | bearing section |
| 46 | bearing portion |
| 47 | actuation spring |
| 48 | piercing part |
| 49 | piercing tip |
| 50 | foil |
| 51 | indention |
| 52 | driving part |
| 53 | bottom |
| 54 | insertion opening |
| 55 | support structure |
| 56 | flexible arm |
| 57 | groove |
| 58 | ratchet |
| 59 | surface |
| 60 | protrusion |
| 61 | blocking part |
| 62 | control portion |
| 63 | control part |
| 64 | retaining nose |
| 65 | retaining recess |
| 66 | locking element |
| 67 | locking spring |
| 68 | pocket |
| 69 | engagement portion |
| 70 | cover |
| 71 | actuator |
| 72 | sliding guide |
| 73 | base portion |

What is claimed is:

1. A nebulizer (1) for a fluid (2), comprising;

a replaceable container (3) containing the fluid (2);

a nebulizer housing (24) for receiving the container (3);

a housing part (18) which is at least one of detachable from the nebulizer (1) and openable for replacing the container (3); and an indicator device (25) for at least one of counting, indicating a number of uses performed, and indicating a number of uses still possible with the container (3);

wherein at least one of:

the indicator device (25) is adapted to initiate at least partial opening of at least one of the nebulizer housing (24) and the housing part (18) in a locked state when a predetermined number of uses has been at least one of reached and exceeded with this container (3), the indicator device (25) is adapted to prevent complete closed assembly of the nebulizer housing (24), housing part (18) and container (3) in a locked state when the predetermined number of uses has been at least one of reached and exceeded with this container (3), and the indicator device (25) is adapted to at least one of block complete inserting of the container (3) into the nebulizer (1), and block complete axial or stroke-like movability of the container (3) in the nebulizer (1) in a locked state when the predetermined number of uses has been at least one of reached and exceeded with this container (3).

2. The nebulizer according to claim 1, wherein the nebulizer (1) is adapted to block at least one of further use and tensioning when at least one of the nebulizer housing (24) and housing part (18) is at least partially open.

3. The nebulizer according to claim 1, wherein the indicator device (25) comprises an indicator element (35) and an actuation element (36) for indexing the indicator element (35).

4. The nebulizer according to claim 3, wherein the actuation element (36) is constructed to block further use of the container (3) in the nebulizer (1) in the locked state, wherein the actuation element (36) is moveable back and forth between a first and second position for indexing the indicator element (35) and is moveable into a third position to block further use of the container (3) in the locked state.

5. The nebulizer according to claim 3, wherein the actuation element (36) at least one of comprises and is formed by a sliding carriage.

6. The nebulizer according to claim 3, wherein the actuation element (36) at least one of blocks and closes an insertion opening (54) of the indicator device (25) in the locked state.

7. The nebulizer according to claim 6, wherein the insertion opening (54) allows insertion of a stationary driving part (52) of the nebulizer (1) when the insertion opening (54) is not at least one of blocked and closed.

8. The nebulizer (1) for a fluid (2), according to claim 1, the nebulizer (1), wherein at least one of:
the indicator device (25) comprises an indicator element (35) and an actuation element (36) for indexing the indicator element (35);
the actuation element (36) is constructed to block further use of the container (3) in a locked state when the predetermined number of uses has been at least one of reached and exceeded with the container (3), and
the actuation element (36) is moveable back and forth between a first and second position for indexing the indicator element (35) and is moveable into a third position to prevent further use of the container (3) in a locked state when the predetermined number of uses has been at least one of reached and exceeded with the container (3).

9. The nebulizer according to claim 1, wherein the indicator device (25) comprises a blocking part (61) which blocks further use of the container (3) in the nebulizer (1) in the locked state, wherein the blocking part (61) is integrated into a housing (31) of the indicator device (25).

10. The nebulizer according to claim 9, wherein the blocking part (61) at least one of blocks and closes an insertion opening (54) of the indicator device (25) in the locked state.

11. The nebulizer according to claim 10, wherein the blocking part (61) at least one of comprises and is formed by a sliding carriage.

12. The nebulizer according to claim 9, wherein the blocking part (61) is at least one of connected with and forms an actuation arm (38) for indexing an indicator element (35) of the indicator device (25).

13. The nebulizer (1) for a fluid (2), according to claim 1, wherein the nebulizer (1), wherein at least one of:
the indicator device (25) comprises a blocking part (61) for preventing further use of the container (3) in a locked state when the predetermined number of uses has been at least one of reached and exceeded with the container (3);
the blocking part (61) closes an insertion opening (54) of the indicator device (25) in the locked state; and
the blocking part (61) is at least one of integrated into a housing (31) of the indicator device (25) and is moveable transversally to at least one of a longitudinal and dispensing direction of at least one of the container (3) and nebulizer (1).

14. The nebulizer according to claim 1, wherein the nebulizer (1) comprises a stationary driving part (52) for at least one of:
(i) at least one of driving, actuating, and triggering the indicator device (25), and; and
(ii) at least one of opening and piercing the container (3), by relative movement of at least one of the container (3) and indicator device (25) to at least one of the nebulizer housing (24) and the driving part (25).

15. The nebulizer according to claim 1, wherein the indicator device (25) is inseparably connected with of the container (3), but separable from the nebulizer housing (24) and housing part (18), so that it is replaceable together with the container (3).

16. The nebulizer (1) for a fluid (2), according to claim 1, the nebulizer (1), wherein:
the container (3) is moveable axially within the closed nebulizer housing (24) during nebulization, and
the indicator device (25) comprises a housing (31) which is inseparably connected with a housing (29) of the container (3), but separable from the nebulizer housing (24) and housing part (18), so the indicator device (25) is replaceable together with the container (3).

17. The nebulizer according to claim 1, wherein at least one of:
the indicator device (25) is fixedly arranged at at least one of a base (21) of the container (3) and opposite to an outlet or head (28) of the container (3), and
the indicator device (25) is connected by snap-fit and form-fit with the container (3).

18. The nebulizer according to claim 1, wherein the indicator device (25) comprises a piercing part (48) for opening an aeration of the container (3).

19. The nebulizer according to claim 18, wherein the piercing part (48) is at least one of axially moveable inside, is located inside, and biased inside a housing (31) of the indicator device (25), when not actuated.

20. A container (3) for a nebulizer (1), the container (3) containing a fluid (2), and the container (3) comprising:
an indicator device (25) for at least one of counting and indicating at least one of a number of uses performed and a number of uses still possible with the container (3),
wherein the indicator device (25) comprises a piercing part (48) for opening an aeration of the container (3).

21. The container according to claim 20, wherein the indicator device (25) is fixedly arranged at least one of at a base (21) of the container (3) and opposite to at least one of an outlet and head (28) of the container 3.

22. The container according to claim 20, wherein the indicator device (25) is connected by at least one of a snap-fit and a form-fit with the container (3).

23. The container according to claim 20, wherein the indicator device (25) comprises an indicator element (35) and an actuation element (36) for indexing the indicator element (35), wherein the actuation element (36) is constructed to block further use of the container (3) in a locked state when a predetermined number of uses has been at least one of reached and exceeded with the container (3).

24. The container according to claim 21, wherein the indicator device (25) comprises a blocking part (61) which blocks further use of the container (3) in a locked state when a predetermined number of uses has been at least one of reached and exceeded with the container (3), wherein the blocking part (61) closes an insertion opening (54) of the indicator device (25) in the locked state.

25. A container (3) for a nebulizer (1), the container (3) containing a fluid (2), and the container (3) comprising:
   an indicator device (25) for at least one of counting and indicating at least one of a number of uses performed and a number of uses still possible with the container (3), wherein at least one of:
   the indicator device (25) comprises an indicator element (35) and an actuation element (36) for indexing the indicator element (35),
   the actuation element (36) is constructed to block further use of the container (3) in a locked state when a predetermined number of uses has been at least one of reached and exceeded with the container (3), and
   the actuation element (36) is moveable back and forth between a first and second position for indexing the indicator element (35) and is moveable into a third position to block further use of the container (3) in a locked state when the predetermined number of uses has been at least one of reached and exceeded with the container (3).

26. The container according to claim 25, wherein the actuation element (36) at least one of comprises and is formed by a sliding carriage.

27. The container according to claim 25, wherein the actuation element (36) closes an insertion opening (54) of the indicator device (25) in the locked state.

28. A container (3) for a nebulizer (1), the container (3) containing a fluid (2), and the container (3) comprising:
   an indicator device (25) for at least one of counting and indicating at least one of a number of uses performed and a number of uses still possible with the container (3), wherein at least one of:
   the indicator device (25) comprises a blocking part (61) which blocks further use of the container (3) in a locked state when a predetermined number of uses has been at least one of reached and exceeded with the container (3),
   the blocking part (61) closes an insertion opening (54) of the indicator device (25) in the locked state, and
   the blocking part (61) is at least one of integrated into a housing (31) of the indicator device (25) and moveable transversally to at least one of a longitudinal and dispensing direction of the container (3).

29. The container according to claim 28, wherein the blocking part (61) is connected with an actuation arm (38) for indexing an indicator element (35).

30. The container according to claim 28, wherein the blocking part (61) at least one of comprises and is formed by a sliding carriage.

* * * * *